(12) United States Patent
Chen et al.

(10) Patent No.: US 10,336,803 B2
(45) Date of Patent: *Jul. 2, 2019

(54) INSULIN SECRETING POLYPEPTIDES

(71) Applicant: Mayo Foundation for Medical Education and Research, Rochester, MN (US)

(72) Inventors: Horng H. Chen, Rochester, MN (US); John C. Burnett, Jr., Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/933,079

(22) Filed: Mar. 22, 2018

(65) Prior Publication Data

US 2018/0273600 A1    Sep. 27, 2018

Related U.S. Application Data

(63) Continuation of application No. 14/767,228, filed as application No. PCT/US2014/016244 on Feb. 13, 2014, now Pat. No. 9,938,334.

(60) Provisional application No. 61/765,276, filed on Feb. 15, 2013.

(51) Int. Cl.
    *C07K 14/605* (2006.01)
    *A61K 38/00* (2006.01)

(52) U.S. Cl.
    CPC ............ *C07K 14/605* (2013.01); *A61K 38/00* (2013.01)

(58) Field of Classification Search
    CPC .................................................. C07K 14/605
    See application file for complete search history.

(56) References Cited

U.S. PATENT DOCUMENTS

| | | | |
|---|---|---|---|
| 5,580,859 A | 12/1996 | Felgner et al. | |
| 5,589,466 A | 12/1996 | Felgner et al. | |
| 8,076,288 B2 | 12/2011 | Levy et al. | |
| 2004/0086976 A1 | 5/2004 | Fleer et al. | |
| 2010/0041612 A1 | 2/2010 | Beinborn | |
| 2010/0048468 A1* | 2/2010 | Gegg, Jr. ............. | C07K 14/605 514/11.7 |
| 2011/0053787 A1 | 3/2011 | Brulliard et al. | |

FOREIGN PATENT DOCUMENTS

| | | |
|---|---|---|
| CN | 1219134 | 6/1999 |
| EP | 0911034 | 4/1999 |
| JP | A-2009-534423 | 9/2009 |
| JP | A-2011-246468 | 12/2011 |
| WO | WO 2007/017892 | 2/2007 |
| WO | WO 2007/124461 | 11/2007 |
| WO | WO 2010/041612 | 4/2010 |
| WO | WO 2010/125079 | 11/2010 |

OTHER PUBLICATIONS

Y. Feng et al. / Biomedicine & Pharmacotherapy 84 (2016) 1826-1832 (Year: 2016).*
Ausubel et al., Ed., *Short Protocols in Molecular Biology*, Chapter 8, 1992, 26 pages.
Cataliotti et al., "Oral brain natriuretic peptide: a novel strategy for chronic protein therapy for cardiovascular disease," *Trends Cardiovasc Med.*, 17(1):10-14, Jan. 2007.
Chinese Office Action for Chinese Application No. 201480019420.2, dated Dec. 29, 2016, 6 pages with English translation.
Chinese Office Action for Chinese Application No. 201480019420.2, dated Jun. 7, 2017, 3 pages (with English translation).
Donnelly., "The structure and function of the glucagon-like peptide-1 receptor and its ligands," *Br J Pharmacol.*, 166:27-41, 2012.
European Office Action for European Application No. EP14751532.4, dated Apr. 3, 2017, 4 pages.
European Search Report for Application No. 14751532, dated Jul. 4, 2016, 7 pages.
Fan et al., Exendin-4 Improves Blood Glucose Control in Both Young and Aging Normal Non-Diabetic Mice, Possible Contribution of Beta Cell Independent Effects, PLoS ONE, May 2011, vol. 6, Issue 5 I e20443, 9 pages.
Green et al., "Structurally modified analogues of glucagon-like peptide-1 (GLP-1) and glucose-dependent insulinotropic polypeptide (GIP) as future antidiabetic agents," *Curr Pharm Des.*, 10(29):3651-3662, 2004.
Guatelli et al., "Isothermal, in vitro amplification of nucleic acids by a multienzyme reaction modeled after retroviral replication," *Proc Natl Acad Sci U S A.*, 87(5):1874-1878, Mar. 1990.
International Preliminary Report on Patentability for PCT/US2014/016244, dated Aug. 18, 2015, 8 pages.
International Search Report for PCT/US2014/016244 dated May 12, 2014, 18 pages.
Japanese Office Action in the International Application No. JP2015-558127, dated Dec. 28, 2017, 9 pages (with English Translation).
Japanese Office Action in the International Application No. JP2015-558127, dated Mar. 27, 2018, 10 pages (with English Translation).
Kjems et al., "The influence of GLP-1 on glucose-stimulated insulin secretion: effects on beta-cell sensitivity in type 2 and nondiabetic subjects," *Diabetes*, 52(2):380-386, Feb. 2003.
Lewis, "PCR's Competitors Are Alive and Well and Moving Rapidly Towards Commercialization," *Genetic Engineering News* 12:1, 1992, 3 pages.
Miller et al., "Amphiphilic conjugates of human brain natriuretic peptide designed for oral delivery: in vitro activity screening," *Biconjug Chem.*, 17(2):267-274, Mar.-Apr. 2006.
Montrose-Rafizadeh et al., "High Potency Antagonists of the Pancreatic Glucagon-like Peptide-1 Receptor," *J Biol Chem.*, 272(34):21201-21206, 1997.
PCR Primer: A Laboratory Manual, ed. By Dieffenbach and Dveksler, Cold Spring Harbor Laboratory Press, 1995, [table of contents], 6 pages.

(Continued)

*Primary Examiner* — Karlheinz R. Skowronek
*Assistant Examiner* — Joseph Fischer
(74) *Attorney, Agent, or Firm* — Fish & Richardson P.C.

(57) ABSTRACT

This document provides methods and materials related to insulin secreting polypeptides. For example, polypeptides having the ability to induce insulin secretion and methods and materials for using use such polypeptides to induce insulin secretion and to treat diabetes are provided.

2 Claims, 19 Drawing Sheets

Specification includes a Sequence Listing.

(56) References Cited

OTHER PUBLICATIONS

Sambrook et al., Molecular Cloning: A Laboratory Manual (2nd edition), Cold Spring Harbor Laboratory, New York (1989) [table of contents] 23 pages.
Tsuruda et al., "Brain natriuretic Peptide is produced in cardiac fibroblasts and induces matrix metalloproteinases," *Circ Res.*, 91(12):1127-1134, Dec. 13, 2002.
Underwood et al., "Crystal structure of glucagon-like peptide-1 in complex with the extracellular domain of the glucagon-like peptide-1 Receptor," *Jour Biol Chem.*, 285(1): 723-730, Jan. 1, 2010.
Veronese and Mero, "The impact of PEGylation on biological therapies," *BioDrugs.*, 22(5):315-329, 2008.
Veronese and Pasut, "PEGylation, successful approach to drug delivery," *Drug Discov Today.*, 10(21):1451-1458, Nov. 1, 2005.
Wang et al., "AlbuBNP, a recombinant B-type natriuretic peptide and human serum albumin fusion hormone, as a long-term therapy of congestive heart failure," *Pharm Res.*, 21(11):2105-2111, Nov. 2004.
Weiss, "Hot prospect for new gene amplifier," *Science*, 254(5036):1292-1293, Nov. 29, 1991.
Xiao et al., "Biological activities of glucagon-like peptide-1 analogues in vitro and in vivo," *Biochemistry*, 40(9):2860-2869, Mar. 6, 2001.

\* cited by examiner

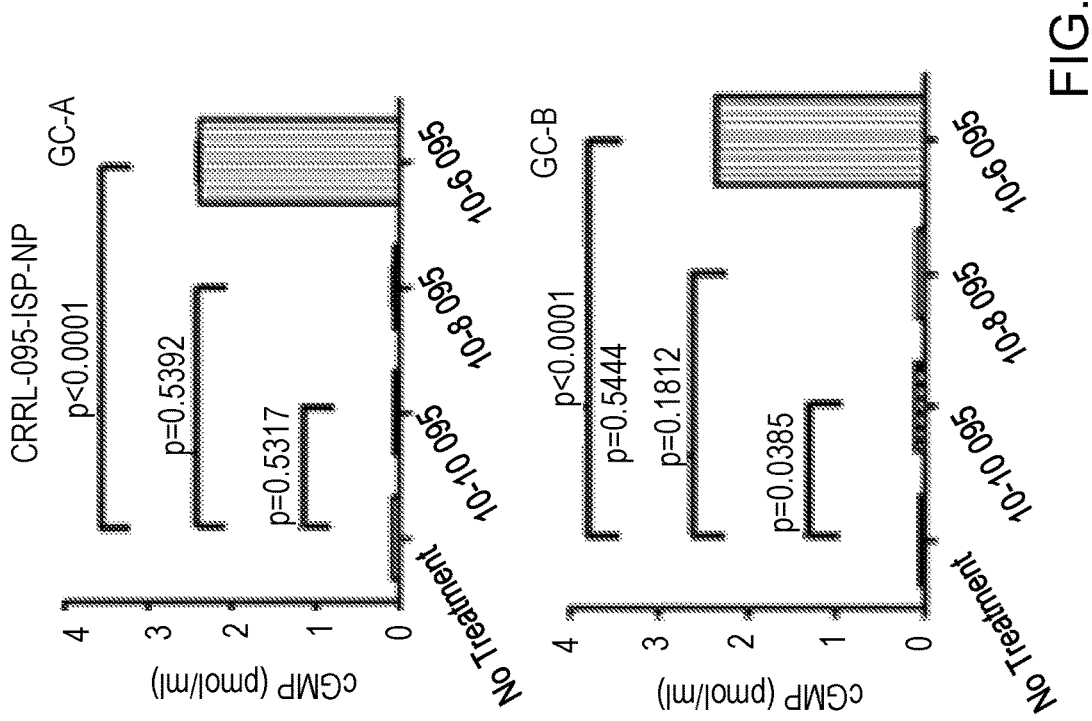
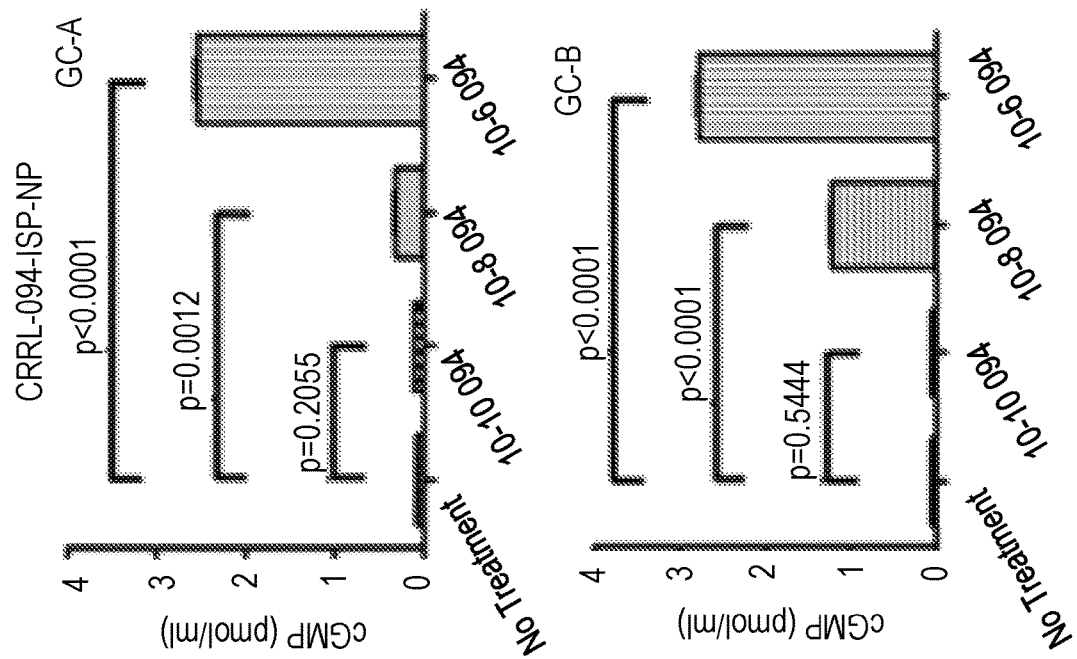
FIG. 15

INSULIN SECRETING POLYPEPTIDES

CROSS-REFERENCE TO RELATED APPLICATIONS

This application is a continuation of U.S. patent application Ser. No. 14/767,228, filed Aug. 11, 2015 (now U.S. Pat. No. 9,938,334), which is a National Stage application under 35 U.S.C. § 371 of International Application No. PCT/US2014/016244, filed Feb. 13, 2014, which claims the benefit of U.S. Provisional Application Serial No. 61/765,276, filed Feb. 15, 2013. The disclosures of the prior applications are considered part of (and are incorporated by reference in) the disclosure of this application.

BACKGROUND

1. Technical Field

This document relates to insulin secreting polypeptides. For example, this document provides methods and materials related to polypeptides having the ability to induce insulin secretion and methods and materials related to the use of such polypeptides to induce insulin secretion and to treat diabetes.

2. Background Information

Diabetes mellitus refers to a group of metabolic diseases where one suffers from high blood sugar. This can be because the pancreas does not produce enough insulin or because cells do not respond to the insulin that is produced. High blood sugar can produce symptoms of frequent urination, increased thirst, and/or increased hunger.

There are three main types of diabetes. Type 1 diabetes results from a failure to produce insulin. Type 2 diabetes results from insulin resistance. The third main form is gestational diabetes, which occurs when pregnant women without a previous diagnosis of diabetes develop a high blood glucose level.

SUMMARY

This document provides methods and materials related to insulin secreting polypeptides. For example, this document provides polypeptides having the ability to induce insulin secretion and methods and materials for using such polypeptides to induce insulin secretion and to treat diabetes.

As described herein, a polypeptide can be designed to include the amino acid sequence set forth in SEQ ID NO:1 (HGEGTFTSDSEAFIWLGR) or the amino acid sequence set forth in SEQ ID NO:1 with the exception that it contains one, two, three, four, or five amino acid additions, subtractions, or substitutions. For example, a polypeptide, referred to herein as CRRL-090 ISP, can be designed to be as follows: HGEGTFTSDSEAFIWLGR-amide. The polypeptides provided herein can have the ability to lower blood glucose, increase plasma insulin, increase glomerular filtration rate (GFR), allow for less left ventricular hypertrophy, and/or improve cardiorenal function when administered to a diabetic mammal. In some cases, a polypeptide provided herein can have glucagon-like peptide-1 (GLP-1) properties.

In general, one aspect of this document features a polypeptide from 15 to 21 amino acid residues in length. The polypeptide comprises, or consists essentially of, the sequence set forth in SEQ ID NO:1 or the sequence set forth in SEQ ID NO:1 with no more than four amino acid additions, subtractions, or substitutions. The polypeptide can comprise a glucagon-like peptide-1 activity. The polypeptide can comprise the sequence set forth in SEQ ID NO:1 with three amino acid additions, subtractions, or substitutions. The polypeptide can comprise the sequence set forth in SEQ ID NO:1 with two amino acid additions, subtractions, or substitutions. The polypeptide can comprise the sequence set forth in SEQ ID NO:1 with one amino acid addition, subtraction, or substitution. The polypeptide can comprise the sequence set forth in SEQ ID NO:1.

In another aspect, this document features a polypeptide from 45 to 55 amino acid residues in length. The polypeptide comprises, or consists essentially of, the sequence set forth in SEQ ID NO:2 or the sequence set forth in SEQ ID NO:2 with no more than four amino acid additions, subtractions, or substitutions. The polypeptide can comprise a glucagon-like peptide-1 activity and/or a particulate guanylate cyclase activating property. The polypeptide can comprise the sequence set forth in SEQ ID NO:2 with three amino acid additions, subtractions, or substitutions. The polypeptide can comprise the sequence set forth in SEQ ID NO:2 with two amino acid additions, subtractions, or substitutions. The polypeptide can comprise the sequence set forth in SEQ ID NO:2 with one amino acid addition, subtraction, or substitution. The polypeptide can comprise the sequence set forth in SEQ ID NO:2.

In another aspect, this document features a polypeptide from 45 to 55 amino acid residues in length. The polypeptide comprises, or consists essentially of, the sequence set forth in SEQ ID NO:3 or the sequence set forth in SEQ ID NO:3 with no more than four amino acid additions, subtractions, or substitutions. The polypeptide can comprise a glucagon-like peptide-1 activity. The polypeptide can comprise the sequence set forth in SEQ ID NO:3 with three amino acid additions, subtractions, or substitutions. The polypeptide can comprise the sequence set forth in SEQ ID NO:3 with two amino acid additions, subtractions, or substitutions. The polypeptide can comprise the sequence set forth in SEQ ID NO:3 with one amino acid addition, subtraction, or substitution. The polypeptide can comprise the sequence set forth in SEQ ID NO:3.

In another aspect, this document features a polypeptide from 30 to 65 (e.g., from 30 to 60, from 30 to 55, from 30 to 50, from 30 to 45, from 30 to 40, from 35 to 65, from 40 to 65, from 45 to 65, from 50 to 65, from 55 to 65, from 35 to 60, from 40 to 60, from 45 to 60, from 50 to 60, from 55 to 60, from 40 to 50, from 45 to 55, from 35 to 45, or from 55 to 65) amino acid residues in length. The polypeptide comprises, or consists essentially of, the sequence set forth in SEQ ID NO:1, 2, 3, 4, 5, 6, 7, 8, 9, 10, 11, 12, 13, 14, 15, 16, 17, or 18 or the sequence set forth in SEQ ID NO:1, 2, 3, 4, 5, 6, 7, 8, 9, 10, 11, 12, 13, 14, 15, 16, 17, or 18 with no more than four amino acid additions, subtractions, or substitutions. The polypeptide can comprise a glucagon-like peptide-1 activity, the ability to increase insulin secretion, and/or a particulate guanylate cyclase activating property. The polypeptide can comprise the sequence set forth in SEQ ID NO:1, 2, 3, 4, 5, 6, 7, 8, 9, 10, 11, 12, 13, 14, 15, 16, 17, or 18 with three amino acid additions, subtractions, or substitutions. The polypeptide can comprise the sequence set forth in SEQ ID NO:1, 2, 3, 4, 5, 6, 7, 8, 9, 10, 11, 12, 13, 14, 15, 16, 17, or 18 with two amino acid additions, subtractions, or substitutions. The polypeptide can comprise the sequence set forth in SEQ ID NO:1, 2, 3, 4, 5, 6, 7, 8, 9, 10, 11, 12, 13, 14, 15, 16, 17, or 18 with one amino acid addition, subtraction, or substitution. The polypeptide can comprise the sequence set forth in SEQ ID NO:1, 2, 3, 4, 5, 6, 7, 8, 9, 10, 11, 12, 13, 14, 15, 16, 17, or 18.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 15 contains graphs plotting the cGMP levels (pmol/mL) for GC-A receptor cells or GC-B receptor cells exposed to no treatment or treatment with $10^{-10}$ M, $10^{-8}$M, or $10^{-6}$M of the CRRL-094 ISP-NP polypeptide or the CRRL-095 ISP-NP polypeptide.

** indicates p<0.05 versus Normal Control; *$$ indicates p<0.05 versus Diabetic Control.

Figure 20:
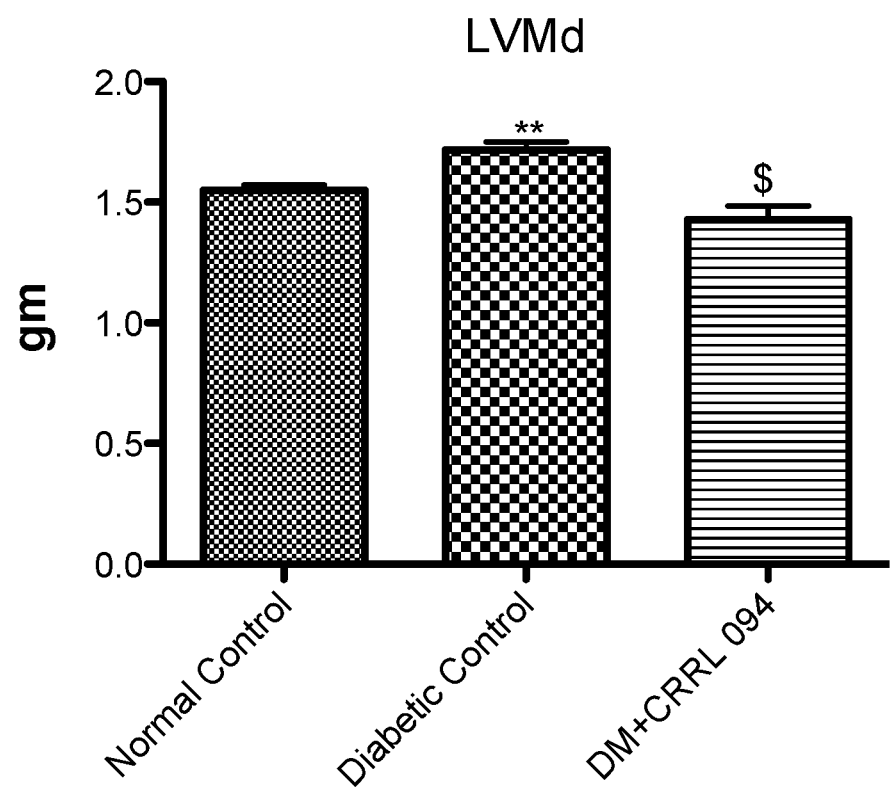

FIG. 20 is a graph plotting Left Ventricular Mass (LVMd; grams) measured in normal non-diabetic control rats treated with saline (normal control), diabetic control rats treated with saline (diabetic control), and diabetic rats treated with CRRL-094 ISP-NP (DM+CRRL 094) after four weeks of saline or CRRL-094 ISP-NP treatment. ** indicates p<0.05 versus Normal Control; $ indicates p<0.05 versus Diabetic Control.

DETAILED DESCRIPTION

This document provides methods and materials related to insulin secreting polypeptides. For example, this document provides polypeptides having the ability to induce insulin secretion and methods and materials for using use such polypeptides to induce insulin secretion and to treat diabetes.

The polypeptides provided herein can be designed to include the amino acid sequence set forth in SEQ ID NO:1 or the amino acid sequence set forth in SEQ ID NO:1 with the exception that it contains one, two, three, four, or five amino acid additions, subtractions, or substitutions. For example, a polypeptide provided herein can be a CRRL-090 ISP polypeptide. In some cases, a polypeptide having the amino acid sequence set forth in SEQ ID NO:1 or the amino acid sequence set forth in SEQ ID NO:1 with the exception that it contains one, two, three, four, or five amino acid additions, subtractions, or substitutions can have the ability to lower blood glucose, increase plasma insulin, increase glomerular filtration rate (GFR), allow for less left ventricular hypertrophy, and/or improve cardiorenal function when administered to a diabetic mammal. In some cases, a polypeptide having the amino acid sequence set forth in SEQ ID NO:1 or the amino acid sequence set forth in SEQ ID NO:1 with the exception that it contains one, two, three, four, or five amino acid additions, subtractions, or substitutions can have glucagon-like peptide-1 (GLP-1) properties.

This document also provides chimeric polypeptides having at least one amino acid segment (e.g., N-terminus tail, ring structure, C-terminus tail, or a combination thereof) of a natriuretic peptide (e.g., ANP, BNP, CNP, URO, or DNP) and an amino acid segment that includes either the amino acid sequence set forth in SEQ ID NO:1 or the amino acid sequence set forth in SEQ ID NO:1 with the exception that it contains one, two, three, four, or five amino acid additions, subtractions, or substitutions. Examples of such chimeric polypeptides provided herein include, without limitation, SPKMVQG-SGCFGRKMDRISSSSGLGCKVLRRH-GEGTFTSDSEAFIWLGR (designated CRRL-092 ISP-NP; SEQ ID NO:2), HGEGTFTSDSEAFIWLGRSPKMVQGS-GCFGRK-MDRISSSSGLGCKVLRRH (designated CRRL-093 ISP-NP; SEQ ID NO:3), HGEGT-FTSDSEAFI-WLGRRMDRIGLSKGCFGLKLDRIGSMSGLGCKVL-RRH (designated CRRL-094 ISP-NP; SEQ ID NO:4), RMDRIGLSKGCFGLKLDRIGSMSG-LGCKVLRRHH-GEGTFTSDSEAFIWLGR (designated CRRL-095 ISP-NP; SEQ ID NO:5), RMDRIGLSKGCFGLKLDRIGSMSGL-GCKVLRRHGEGTFTSDSEAFIWLGR (designated CRRL-096 ISP-NP; SEQ ID NO:6), SLRRSSCFGGRM-DRIGAQSGL-GCNSFRYHGEGTFTSDSEAFIWLGR (designated CRRL-097 ISP-NP; SEQ ID NO:7), HGEGT-FTSDSEAFIWLGRSLRRSSCFGGRMDRIGAQSGL-GCNSFRY (designated CRRL-098 ISP-NP; SEQ ID NO:8), GLSKGCFGLKLDRIGSMSGLGC-HGEGTFTSDSEAFI-WLGR (designated CRRL-099 ISP-NP; SEQ ID NO:9), HGEG-TFTSDSEAFIWLGRGLSKGCFGLKLDRIGSMS-GLGC (designated CRRL-100 ISP-NP; SEQ ID NO:10), EVKYDPCFGHKIDRINHVSNLGCPSLRDPRPNAPSTS-AHGEGTFTSDSEAFIWLGR (designated CRRL-101 ISP-NP; SEQ ID NO:11), HGEG-TFT SDSEAFIWLGREVKY-DPCFGHKIDRINHVSNLGCPSLRDPRPNAPSTSA (designated CRRL-102 ISP-NP; SEQ ID NO:12), TAPRSL-RRSSCFGLKLDRIGS-MSGLGCNSFRYHGEGTFTSD-SEAFIWLGR (designated CRRL-103 ISP-NP; SEQ ID NO:13), HGEGTFTSDSEAFIWLGRTAPRSLRRSSCF-GLKLDRIGSMSGLGCNSFRY (designated CRRL-104 ISP-NP; SEQ ID NO:14), GLSKGCFGLKLDRIGSM-SGLGCPSLRDPRPNAPSTSAHGEGTFTSDSEAFI-WLGR (designated CRRL-105 ISP-NP; SEQ ID NO:15), HGEGTFTSDSEAFIWLGRGLSKGCFGLKLDRIGSMS-GLGCPSLRDPRPNAPSTSA (designated CRRL-106 ISP-NP; SEQ ID NO:16), SLRRSSCFGG-RMDRIGAQSGL-GCNSFRYRITAREDKQGWAHGEGTFTSDSEAFIWLGR (designated CRRL-107 ISP-NP; SEQ ID NO:17), and HGEGTFTSDSEAFIWLGRSLRRSSCFGGRMDRI-GAQSGLGCNSFRYRITAREDKQGWA (designated CRRL-108 ISP-NP; SEQ ID NO:18).

In some cases, a chimeric polypeptide provided herein can be used to lower blood glucose, increase plasma insulin, increase glomerular filtration rate (GFR), allow for less left ventricular hypertrophy, and/or improve cardiorenal function when administered to a diabetic mammal. In some cases, a chimeric polypeptide provided herein can be used to increase natriuretic activity in a subject in need thereof in addition to lowering blood glucose, increasing plasma insulin, increasing glomerular filtration rate (GFR), allowing for less left ventricular hypertrophy, and/or improving cardiorenal function. Examples of natriuretic activities that can be increased using a chimeric polypeptide provided herein include, without limitation, increases in plasma cGMP levels, urinary cGMP excretion, net renal cGMP generation, urine flow, urinary sodium excretion, urinary potassium excretion, hematocrit, plasma BNP immunoreactivity, renal blood flow, and/or plasma ANP immunoreactivity. In some cases, a chimeric polypeptide provided herein can be used to decrease renal vascular resistance, proximal and distal fractional reabsorption of sodium, mean arterial pressure, pulmonary capillary wedge pressure, right atrial pressure, pulmonary arterial pressure, plasma renin activity, plasma angiotensin II levels, plasma aldosterone levels, renal perfusion pressure, and/or systemic vascular resistance. In some cases, a chimeric polypeptide provided herein can be used to treat, inhibit, and/or prevent cardiac remodeling and ischemia-reperfusion injury, particularly after acute myocardial infarction (AMI) and/or acute heart failure (AHF). For example, a chimeric polypeptide provided herein can be used to increase plasma cGMP, which may be desirable for applications in attenuating myocardial ischemia-reperfusion injury (Padilla et al., *Cardiovasc. Res.*, 51:592-600 (2001)).

As described herein, a polypeptide provided herein can be designed to include the amino acid sequence set forth in SEQ ID NO:1 or the amino acid sequence set forth in SEQ ID NO:1 with the exception that it contains one, two, three, four, or five amino acid additions, subtractions, or substitutions. For example, a polypeptide provided herein can be designed to include the amino acid sequence set forth in SEQ ID NO:1 with the exception that it contains one addition, subtraction, or substitution. In some cases, a polypeptide provided herein can be designed to include the amino acid sequence set forth in SEQ ID NO:1 with the exception that it contains three or less additions, subtractions, or substitutions.

As described herein, a chimeric polypeptide provided herein can be designed to include at least one amino acid segment (e.g., N-terminus tail, ring structure, C-terminus tail, or a combination thereof) of a natriuretic peptide and an amino acid segment that includes either the amino acid sequence set forth in SEQ ID NO:1 or the amino acid sequence set forth in SEQ ID NO:1 with the exception that it contains one, two, three, four, or five amino acid additions, subtractions, or substitutions. In some cases, an N-terminus, ring structure, and/or C-terminus of an natriuretic peptide included in a chimeric polypeptide provided herein can include a variant (e.g., a substitution, addition, or deletion) at one or more positions (e.g., one, two, three, four, five, six, seven, eight, nine, or ten positions). Such variant natriuretic peptide sequences, e.g., those having one or more amino acid substitutions relative to a native natriuretic peptide amino acid sequence (e.g., two, three, four, five, six, or more substitutions), can be prepared and modified using standard techniques.

Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenyalanine, glycine for proline, threonine for serine, serine for threonine, tyrosine for tryptophan, phenylalanine for tyrosine, and/or leucine for valine.

Further examples of conservative substitutions that can be made at any position within SEQ ID NO:1 and/or a natriuretic peptide amino acid sequence used to make a polypeptide or chimeric polypeptide provided herein include, without limitation, those set forth in Table 1.

TABLE 1

Examples of conservative amino acid substitutions.

| Original Residue | Exemplary substitutions |
| --- | --- |
| Ala | Val, Leu, Ile |
| Arg | Lys, Gln, Asn |
| Asn | Gln, His, Lys, Arg |
| Asp | Glu |
| Cys | Ser |
| Gln | Asn |
| Glu | Asp |
| Gly | Pro |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, Gln, Asn |
| Met | Leu, Phe, Ile |
| Phe | Leu, Val, Ile, Ala |
| Pro | Gly |
| Ser | Thr |
| Thr | Ser |
| Trp | Tyr |
| Tyr | Trp, Phe, Thr, Ser |
| Val | Ile, Leu, Met, Phe, Ala, Norleucine |

In some cases, SEQ ID NO:1 and/or a natriuretic peptide amino acid sequence used to make a polypeptide or chimeric polypeptide provided herein can include one or more non-conservative substitutions. Non-conservative substitutions typically entail exchanging a member of one of the classes described above for a member of another class. Such production can be desirable to provide large quantities or alternative embodiments of such compounds. Whether an amino acid change results in a functional polypeptide can readily be determined by assaying the specific activity of the peptide variant.

A polypeptide provided herein can have any appropriate length. For example, a polypeptide provided herein can be between 16 and 25 (e.g., between 17 and 25, between 18 and 25, between 19 and 25, between 16 and 24, between 16 and 23, between 16 and 22, between 16 and 20, between 16 and 19, or between 17 and 19) amino acid residues in length. It will be appreciated that a polypeptide with a length of 16 or 25 amino acid residues is a polypeptide with a length between 16 and 25 amino acid residues. A chimeric polypeptides provided herein can have any appropriate length. For example, a chimeric polypeptide provided herein can be between 40 and 60 (e.g., between 40 and 58, between 40 and 56, between 40 and 54, between 40 and 52, between 42 and 60, between 44 and 60, between 46 and 60, between 48 and 60, or between 48 and 52) amino acid residues in length. It will be appreciated that a polypeptide with a length of 40 or 60 amino acid residues is a polypeptide with a length between 40 and 60 amino acid residues.

The polypeptides and chimeric polypeptides provided herein can be assessed for biological activity using any suitable assay including, without limitation, those described herein. For example, the activity of a chimeric polypeptide having a variant natriuretic peptide amino acid sequence as described herein can be evaluated in vitro by measuring its effect on cGMP levels generated by cardiac fibroblasts (CFs) or by testing its ability to suppress proliferation of CFs. Such experiments can be performed, for example, in human CFs (ScienCell, San Diego, Calif.) as described elsewhere (Tsuruda et al., Circ. Res. 91:1127-1134 (2002)). Cells can be exposed to a polypeptide to be assessed (e.g., $10^{11}$ to $10^{-6}$ M), and samples can be assayed for cGMP using a competitive RIA cGMP kit (Perkin-Elmer, Boston, Mass.). For CF proliferation studies, cells can be treated with Cardiotrophin-1 to induce cell proliferation. A chimeric polypeptide to be assessed can be added to the Cardiotrophin-1-stimulated CFs to determine its effect on cell proliferation. Cell proliferation can be detected and measured using, for example, a colormetric bromodeoxyuridine (BrdU) cell proliferation ELISA (Roche, Indianapolis, Ind.).

In some cases, a chimeric polypeptide provided herein with conservative and/or non-conservative substitutions (e.g., with respect to SEQ ID NO:1 or a natural ANP, BNP, CNP, DNP, or URO) can be assessed in vivo by, for example, testing its effects on factors such as insulin secretion, blood glucose levels, pulmonary capillary wedge pressure, right atrial pressure, mean arterial pressure, urinary sodium excretion, urine flow, proximal and distal fractional sodium reabsorption, plasma renin activity, plasma cGMP levels, urinary cGMP excretion, net renal generation of cGMP, glomerular filtration rate, and left ventricular mass in animals. In some cases, such parameters can be evaluated after induced myocardial infarction (e.g., myocardial infarction induced by coronary artery ligation) or induction of diabetes.

In some cases, a polypeptide provided herein can have an amino acid sequence with at least 85% (e.g., 85%, 86%, 87%, 88%, 89%, 90%, 91%, 92%, 93%, 94%, 95%, 96%, 97%, 98%, 99%, or 100%) sequence identity to a reference sequence (e.g., SEQ ID NO:1, 2, 3, 4, 5, 6, 7, 8, 9, 10, 11, 12, 13, 14, 15, 16, 17, or 18). Percent sequence identity is calculated by determining the number of matched positions in aligned amino acid sequences (target amino acid sequence aligned to an identified amino acid sequence), dividing the number of matched positions by the number of amino acids of the identified amino acid sequence (e.g., SEQ ID NO:1), and multiplying by 100. A matched position refers to a position in which identical amino acids occur at the same position in aligned amino acid sequences. Percent sequence identity also can be determined for any nucleic acid sequence.

Percent sequence identity is determined by comparing a target amino acid sequence to the identified amino acid sequence (e.g., SEQ ID NO:1) using the BLAST 2 Sequences (B12seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S. government's National Center for Biotechnology Information web site (ncbi.nlm.nih.gov). Instructions explaining how to use the B12seq program can be found in the readme file accompanying BLASTZ.

B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\B12seq c:\seq1.txt -j c:\seq2.txt -p blastn -o c:\output.txt -q −1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

For example, if (1) a target sequence is compared to the sequence set forth in SEQ ID NO:1 and (2) the B12seq program presents the target sequence aligned with a region of the sequence set forth in SEQ ID NO:1 with the number of matches being 17, then the amino acid target sequence has a percent identity to SEQ ID NO:1 that is 94.4 (i.e., 17±18×100=94.4). It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

A polypeptide or chimeric polypeptide provided herein can be produced using any suitable method, including solid phase synthesis, and can be generated using manual techniques or automated techniques (e.g., using an Applied BioSystems (Foster City, Calif.) Peptide Synthesizer or a Biosearch Inc. (San Rafael, Calif.) automatic peptide synthesizer). Disulfide bonds between cysteine residues can be introduced by mild oxidation of the linear polypeptides using KCN as described elsewhere (U.S. Pat. No. 4,757,048). In some cases, a polypeptide or chimeric polypeptide provided herein can be produced recombinantly, as described herein.

In some cases, a polypeptide or chimeric polypeptide provided herein can be a substantially pure polypeptide. As used herein, the term "substantially pure" with reference to a polypeptide means that the polypeptide is substantially free of other polypeptides, lipids, carbohydrates, and nucleic acid. In some cases, a substantially pure polypeptide can be a polypeptide that is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

Salts of carboxyl groups of a polypeptide or chimeric polypeptide provided herein can be prepared by contacting the polypeptide with one or more equivalents of a desired base such as, for example, a metallic hydroxide base (e.g., sodium hydroxide), a metal carbonate or bicarbonate base (e.g., sodium carbonate or sodium bicarbonate), or an amine base (e.g., triethylamine, triethanolamine, and the like). Acid addition salts of a polypeptide or chimeric polypeptide provided herein can be prepared by contacting the polypeptide with one or more equivalents of an inorganic or organic acid (e.g., hydrochloric acid).

Esters of carboxyl groups of a polypeptide or chimeric polypeptide provided herein can be prepared using any suitable means for converting a carboxylic acid or precursor to an ester. For example, one method for preparing esters of a polypeptide or chimeric polypeptide provided herein, when using the Merrifield synthesis technique, is to cleave the completed polypeptide from the resin in the presence of the desired alcohol under either basic or acidic conditions, depending upon the resin. The C-terminal end of the polypeptide then can be directly esterified when freed from the resin, without isolation of the free acid.

Amides of a polypeptide or chimeric polypeptide provided herein can be prepared using techniques for converting a carboxylic acid group or precursor to an amide. One method for amide formation at the C-terminal carboxyl group includes cleaving the polypeptide from a solid support with an appropriate amine, or cleaving in the presence of an alcohol, yielding an ester, followed by aminolysis with the desired amine.

N-acyl derivatives of an amino group of a polypeptide or chimeric polypeptide provided herein can be prepared by utilizing an N-acyl protected amino acid for the final condensation, or by acylating a protected or unprotected polypeptide. O-acyl derivatives can be prepared for example, by acylation of a free hydroxy peptide or peptide resin. Either acylation may be carried out using standard acylating reagent such as acyl halides, anhydrides, acyl imidazoles, and the like. Both N- and O-acylation may be carried out together, if desired.

In some cases, a polypeptide or chimeric polypeptide provided herein can be modified by linkage to a polymer such as polyethylene glycol (PEG), or by fusion to another polypeptide such as albumin, for example. For example, one or more PEG moieties can be conjugated to a polypeptide or chimeric polypeptide provided herein via lysine residues. Linkage to PEG or another suitable polymer, or fusion to albumin or another suitable polypeptide can result in a modified polypeptide or chimeric polypeptide having an increased half life as compared to an unmodified polypeptide or chimeric polypeptide. Without being bound by a particular mechanism, an increased serum half life can result from reduced proteolytic degradation, immune recognition, or cell scavanging of the modified polypeptide or chimeric polypeptide. Any appropriate method can be used to modify a polypeptide or chimeric polypeptide provided herein by linkage to PEG (also referred to as "PEGylation") or other polymers including, without limitation, those described elsewhere (U.S. Pat. No. 6,884,780; Cataliotti et al., *Trends Cardiovasc. Med.*, 17:10-14 (2007); Veronese and Mero, *BioDrugs*, 22:315-329 (2008); Miller et al., *Bioconjugate Chem.*, 17:267-274 (2006); and Veronese and Pasut, *Drug Discov. Today*, 10:1451-1458 (2005). Examples of methods for modifying a polypeptide or chimeric polypeptide provided herein by fusion to albumin include, without limitation, those described elsewhere (U.S. Patent Publication No. 20040086976, and Wang et al., *Pharm. Res.*, 21:2105-2111 (2004)).

Nucleic Acids, Vectors, and Host Cells

This document also provides nucleic acids encoding a polypeptide or chimeric polypeptide provided herein, as well as expression vectors containing the nucleic acids, and host cells containing the nucleic acids and/or expression vectors. As used herein, the term "nucleic acid" refers to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids include, for example, cDNAs encoding the chimeric polypeptides provided herein.

An "isolated nucleic acid" is a nucleic acid that is separated from other nucleic acid molecules that are present in a vertebrate genome, including nucleic acids that normally flank one or both sides of the nucleic acid in a vertebrate genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing a nucleotide sequence that encodes a natriuretic polypeptide. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids (e.g., nucleic acids encoding a polypeptide or chimeric polypeptide provided herein) also can be obtained by mutagenesis. For example, a reference sequence can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992.

Sources of nucleotide sequences from which nucleic acid molecules encoding a natriuretic polypeptide, or the nucleic acid complement thereof, can be obtained include total or polyA+ RNA from any eukaryotic source, including reptilian (e.g., snake) or mammalian (e.g., human, rat, mouse, canine, bovine, equine, ovine, caprine, or feline) cellular source from which cDNAs can be derived by methods known in the art. Other sources of the nucleic acid molecules include genomic libraries derived from any eukaryotic cellular source, including mammalian sources.

Nucleic acid molecules encoding native natriuretic polypeptides can be identified and isolated using standard methods, e.g., as described by Sambrook et al., *Molecular Cloning: A Laboratory Manual*, Cold Spring Harbor Laboratory Press, NY (1989). For example, reverse-transcriptase PCR (RT-PCR) can be used to isolate and clone natriuretic polypeptide cDNAs from isolated RNA that contains RNA sequences of interest (e.g., total RNA isolated from human tissue). Other approaches to identify, isolate, and clone natriuretic polypeptide cDNAs include, for example, screening cDNA libraries.

Vectors containing nucleic acids such as those described herein also are provided. A "vector" is a replicon, such as a plasmid, phage, or cosmid, into which another DNA segment may be inserted so as to bring about the replication of the inserted segment. An "expression vector" is a vector that includes one or more expression control sequences, and an "expression control sequence" is a DNA sequence that controls and regulates the transcription and/or translation of another DNA sequence.

In the expression vectors, a nucleic acid (e.g., a nucleic acid encoding a polypeptide or chimeric polypeptide provided herein) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

This document also provides host cells containing a nucleic acid or vector provided herein. The term "host cell" is intended to include prokaryotic and eukaryotic cells into which a recombinant nucleic acid or vector (e.g., an expression vector) can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Suitable methods for transforming and transfecting host cells can be found, for example, in Sambrook et al., *Molecular Cloning: A Laboratory Manual* ($2^{nd}$ edition), Cold Spring Harbor Laboratory, New York (1989). For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Compositions and Methods for Administration

A polypeptide or chimeric polypeptide provided herein (e.g., CRRL-090 ISP), or a nucleic acid encoding a polypeptide or chimeric polypeptide provided herein, can be incorporated into a composition for administration to a mammal (e.g., a human suffering from diabetes or at risk for diabetes). Methods for formulating and subsequently administering therapeutic compositions are well known to those in the art. Dosages typically are dependent on the responsiveness of the subject to the compound, with the course of treatment lasting from several days to several months, or until a suitable response is achieved. Persons of ordinary skill in the art routinely determine optimum dosages, dosing methodologies, and repetition rates. Optimum dosages can vary depending on the relative potency of a polypeptide or chimeric polypeptide provided herein, and generally can be estimated based on the $EC_{50}$ found to be effective in in vitro and/or in vivo animal models. Compositions containing a polypeptide or chimeric polypeptide provided herein (e.g., CRRL-090 ISP) or a nucleic acid provided herein may be given once or more daily, weekly, monthly, or even less often, or can be administered continuously for a period of time (e.g., hours, days, or weeks). For example, a polypeptide or chimeric polypeptide provided herein (e.g., CRRL-090 ISP) or a composition containing a polypeptide or chimeric polypeptide provided herein (e.g., CRRL-090 ISP) can be administered to a diabetic patient at a dose of at least about 0.01 ng polypeptide/kg to about 100 mg polypeptide/kg of body mass, or can be administered continuously as an infusion beginning at a particular time and continuing for one to seven days (e.g., at a dose of about 0.01 ng polypeptide/kg/minute to about 0.5 µg polypeptide/kg/minute).

The polypeptide or chimeric polypeptide provided herein (e.g., CRRL-090 ISP) or nucleic acid provided herein can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption.

In some embodiments, a composition can contain a polypeptide or chimeric polypeptide provided herein (e.g., CRRL-090 ISP) in combination with a pharmaceutically acceptable carrier. Pharmaceutically acceptable carriers include, for example, pharmaceutically acceptable solvents, suspending agents, or any other pharmacologically inert vehicles for delivering antibodies to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing a polypeptide or chimeric polypeptide provided herein (e.g., CRRL-090 ISP) can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols), or can occur by a combination of such methods. Administration can be rapid (e.g., by injection) or can occur over a period of time (e.g., by slow infusion or administration of slow release formulations).

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the other components within the compositions (e.g., a polypeptide or chimeric polypeptide provided herein such as CRRL-090 ISP).

In some cases, a polypeptide or chimeric polypeptide provided herein (e.g., CRRL-090 ISP) can be formulated as a sustained release dosage form. In some cases, coatings, envelopes, or protective matrices can be formulated to contain one or more of the polypeptides or chimeric polypeptides provided herein. Such coatings, envelopes, and protective matrices can be used to coat indwelling devices such as stents, catheters, and peritoneal dialysis tubing. In some cases, a polypeptide or chimeric polypeptide provided herein (e.g., CRRL-090 ISP) can be incorporated into a polymeric substances, liposomes, microemulsions, microparticles, nanoparticles, or waxes.

Pharmaceutical formulations as disclosed herein, which can be presented conveniently in unit dosage form, can be prepared according to conventional techniques well known in the pharmaceutical industry. Such techniques include the step of bringing into association an active ingredient (e.g., a polypeptide or chimeric polypeptide provided herein such as CRRL-090 ISP) with the desired pharmaceutical carrier(s). Typically, the formulations can be prepared by uniformly and intimately bringing an active ingredient into association with liquid carriers or finely divided solid carriers or both, and then, if necessary, shaping the product. Formulations can be sterilized if desired, provided that the method of sterilization does not interfere with the effectiveness of the molecules(s) contained in the formulation (e.g., a polypeptide or chimeric polypeptide provided herein).

Methods for Increasing Insulin Secretion or Treating Diabetes

This document also provides for the use of a polypeptide or chimeric polypeptide provided herein for treatment of, for example, diabetes. For example, a polypeptide or chimeric polypeptide provided herein can be administered to a mammal (e.g., a human or a non-human mammal) in order to increase insulin secretion. In some embodiments, for example, a polypeptide or chimeric polypeptide provided herein or a composition provided herein can be administered to a mammal diagnosed as having diabetes. The polypeptide or chimeric polypeptide provided herein or composition can be administered at any suitable dose, depending on various factors including, without limitation, the agent chosen, the severity of the disease, and whether prevention or treatment is to be achieved. Administration can be local or systemic.

In some embodiments, a polypeptide or chimeric polypeptide provided herein or a composition containing a polypeptide or chimeric polypeptide provided herein can be administered at a dose of at least about 0.01 ng polypeptide/kg to about 100 mg polypeptide/kg of body mass (e.g., about 10 ng polypeptide/kg to about 50 mg polypeptide/kg, about 20 ng polypeptide/kg to about 10 mg polypeptide/kg, about 0.1 ng polypeptide/kg to about 20 ng polypeptide/kg, about 3 ng polypeptide/kg to about 10 ng polypeptide/kg, or about 50 ng polypeptide/kg to about 100 µg/kg) of body mass, although other dosages also may provide beneficial results. In some cases, a polypeptide or chimeric polypeptide provided herein or a composition containing a polypeptide or chimeric polypeptide provided herein can be administered as a continuous intravenous infusion for a period of time (e.g., from one to seven days such as one, two, three, four, five, six, or seven days). Such a composition can be administered at a dose of, for example, about 0.1 ng polypeptide/kg/minute to about 500 ng polypeptide/kg/minute (e.g., about 0.5 ng polypeptide/kg/minute, about 1 ng polypeptide/kg/minute, about 2 ng polypeptide/kg/minute, about 3 ng polypeptide/kg/minute, about 5 ng polypeptide/kg/minute, about 7.5 ng polypeptide/kg/minute, about 10 ng polypeptide/kg/minute, about 12.5 ng polypeptide/kg/minute, about 15 ng polypeptide/kg/minute, about 20 ng polypeptide/kg/minute, about 25 ng polypeptide/kg/minute, about 30 ng polypeptide/kg/minute, about 50 ng polypeptide/kg/minute, about 100 ng polypeptide/kg/minute, or about 300 ng polypeptide/kg/minute).

In some embodiments, a polypeptide or chimeric polypeptide provided herein or a composition containing a polypeptide or chimeric polypeptide provided herein can be administered via a first route (e.g., intravenously) for a first period of time, and then can be administered via another route (e.g., topically or subcutaneously) for a second period of time. For example, a polypeptide or chimeric polypeptide provided herein or a composition containing a polypeptide or chimeric polypeptide provided herein can be intravenously administered to a mammal (e.g., a human) at a dose of about 0.1 ng polypeptide/kg/minute to about 300 ng polypeptide/kg/minute (e.g., about 1 ng polypeptide/kg/minute to about 15 ng polypeptide/kg/minute, about 3 ng polypeptide/kg/minute to about 10 ng polypeptide/kg/minute, or about 10 ng polypeptide/kg/minute to about 30 ng polypeptide/kg/minute) for one to seven days (e.g., one, two, three, four, five, six, or seven days), and subsequently can be subcutaneously administered to the mammal at a dose of about 10 ng polypeptide/kg/day to about 100 ng polypeptide/kg/day (e.g., about 10 ng polypeptide/kg/day, about 20 ng polypeptide/kg/day, about 25 ng polypeptide/kg/day, about 30 ng polypeptide/kg/day, about 50 ng polypeptide/kg/day, or about 100 ng polypeptide/kg/day) for five to 30 days (e.g., seven, 10, 14, 18, 21, 24, or 27 days).

The methods provided herein can include administering to a mammal an amount of a polypeptide or chimeric polypeptide provided herein or a composition containing a polypeptide or chimeric polypeptide provided herein effective to increase insulin secretion or to reduce a symptom of diabetes.

The invention will be further described in the following example, which does not limit the scope of the invention described in the claims.

EXAMPLE

Example 1

CRRL-090 ISP Reduces Blood Glucose and Increases Insulin Secretion

CRRL-090 ISP was synthesized by direct protein synthesis and tested for biological activity in normal rats as follows. Two groups of normal rats were used. The first group included five normal rats, which were administered normal saline. The second group included seven normal rats, which were administered CRRL-090 (1 pmol/kg/minute for 210 minutes). Both administrations were via intravenous infusion.

Figure 1:
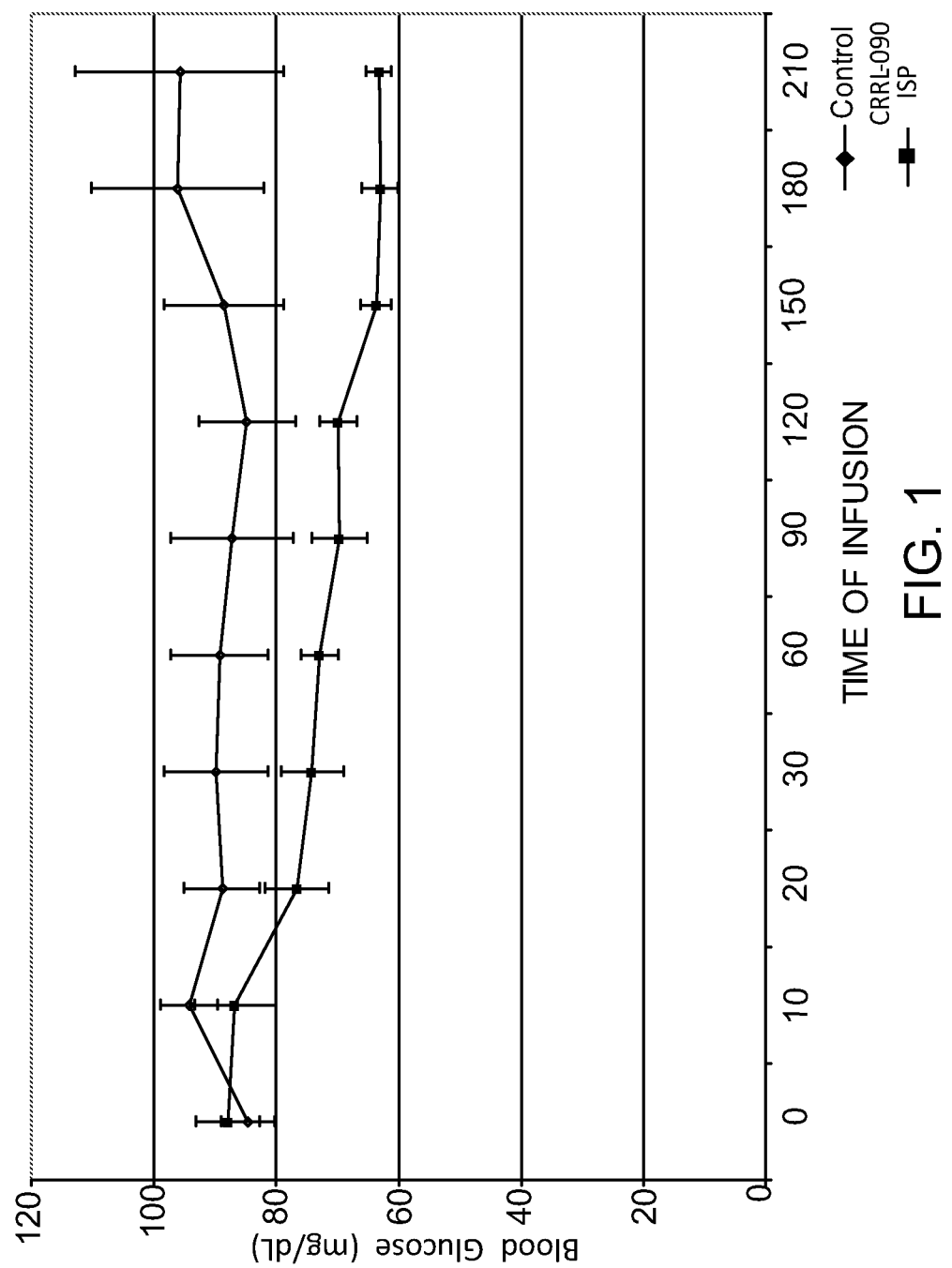
FIG. 1 is a graph plotting the level of blood glucose (mg/dL) measured in control normal rats and normal rats administered CRRL-090 ISP (1 pmol/kg/minute).
Figure 2:
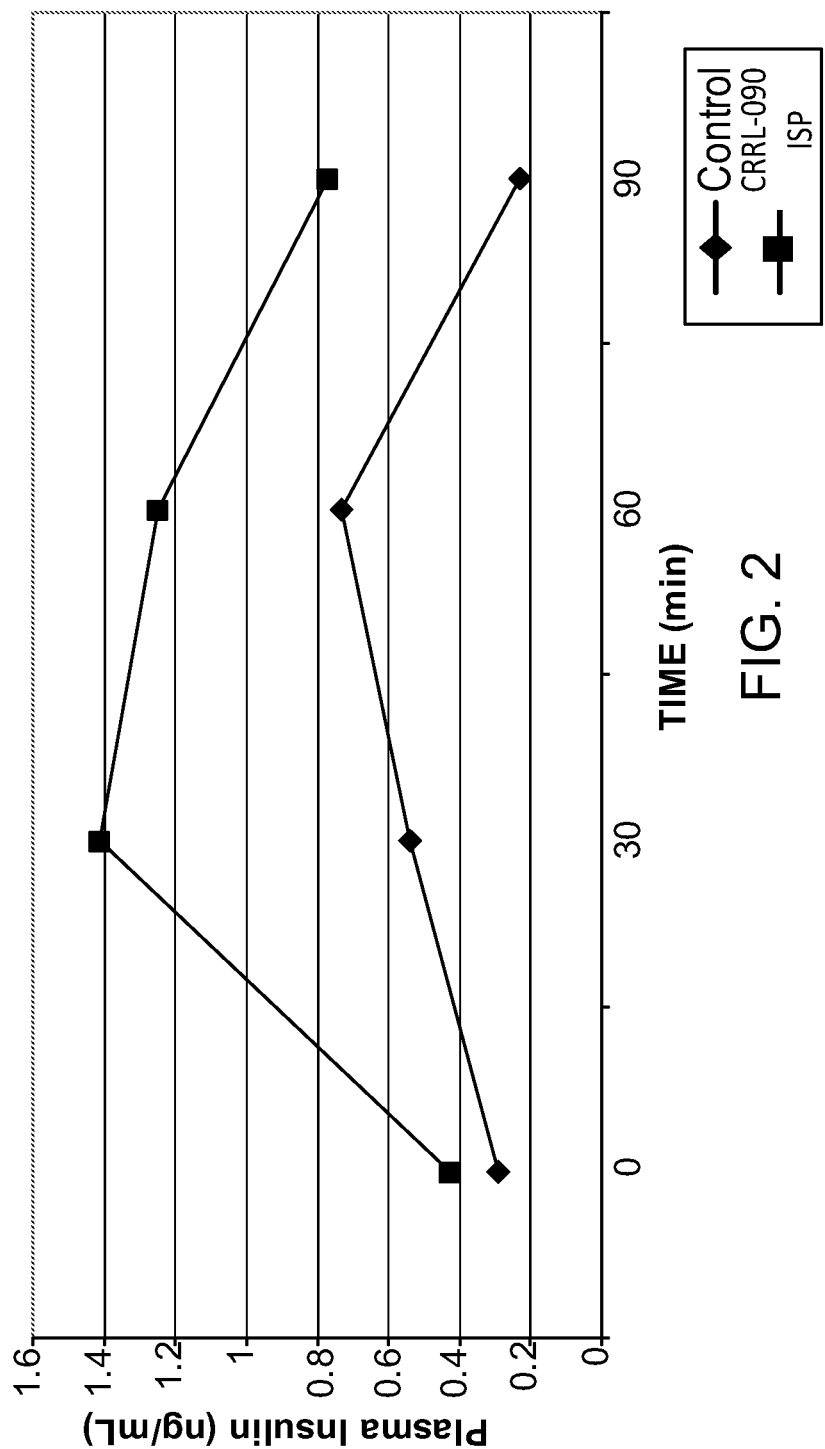
FIG. 2 is a graph plotting the level of plasma insulin (ng/mL) measured in control normal rats and normal rats administered CRRL-090 ISP (1 pmol/kg/minute).
Figure 3:
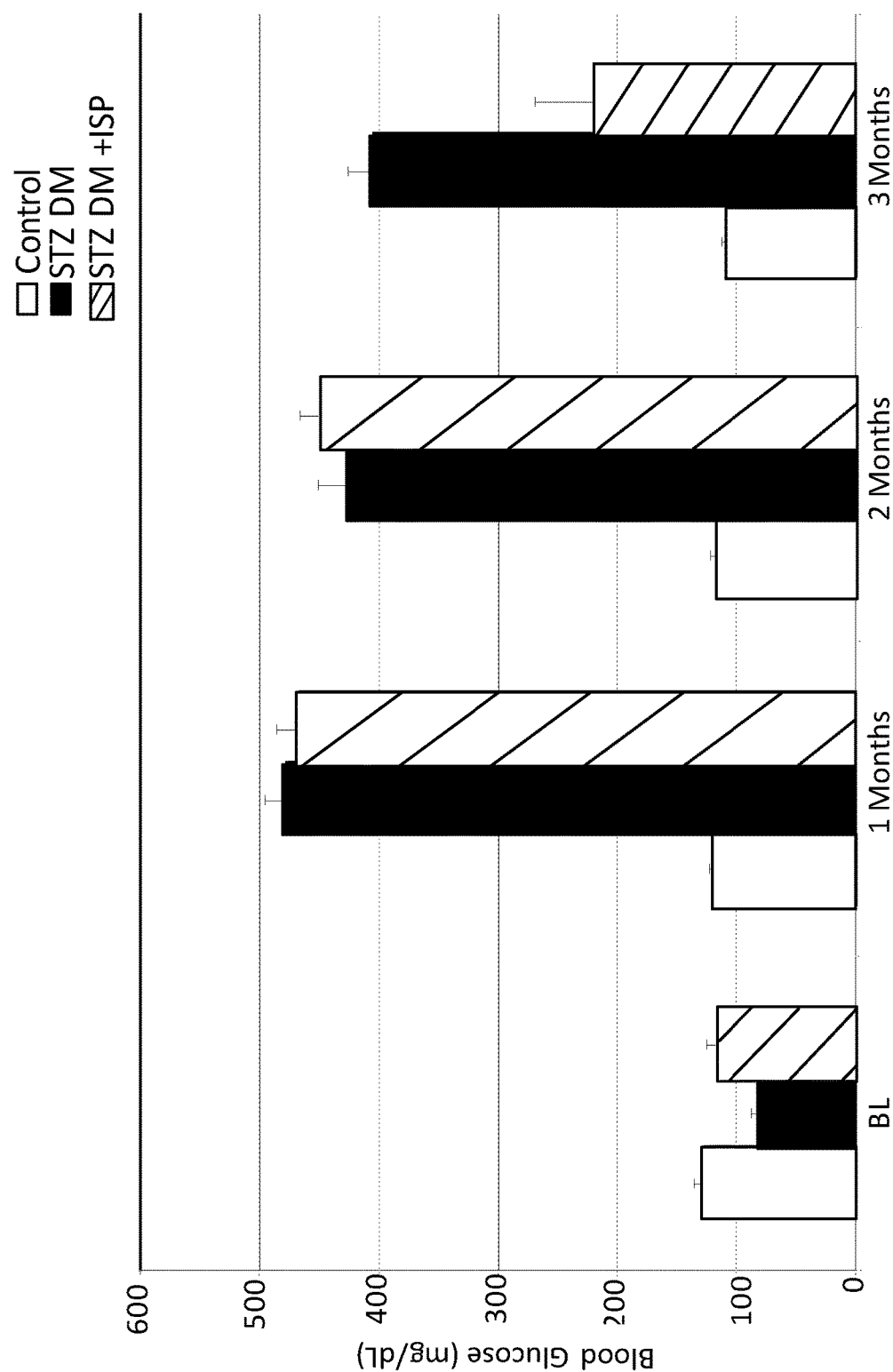
FIG. 3 is a bar graph plotting blood glucose (mg/dL) measured in control normal rats (Control), rats treated with streptozotocin at time zero to induce diabetes (STZ DM), and rats treated with streptozotocin at time zero to induce diabetes followed by treatment with CRRL-090 ISP (1 pmol/kg/minute) for one month starting two months after streptozotocin treatment (STZ DM+ISP). Measurements were made a time zero (background level; BL), one month following streptozotocin treatment, two months following streptozotocin treatment, and three months following streptozotocin treatment.
Figure 4:
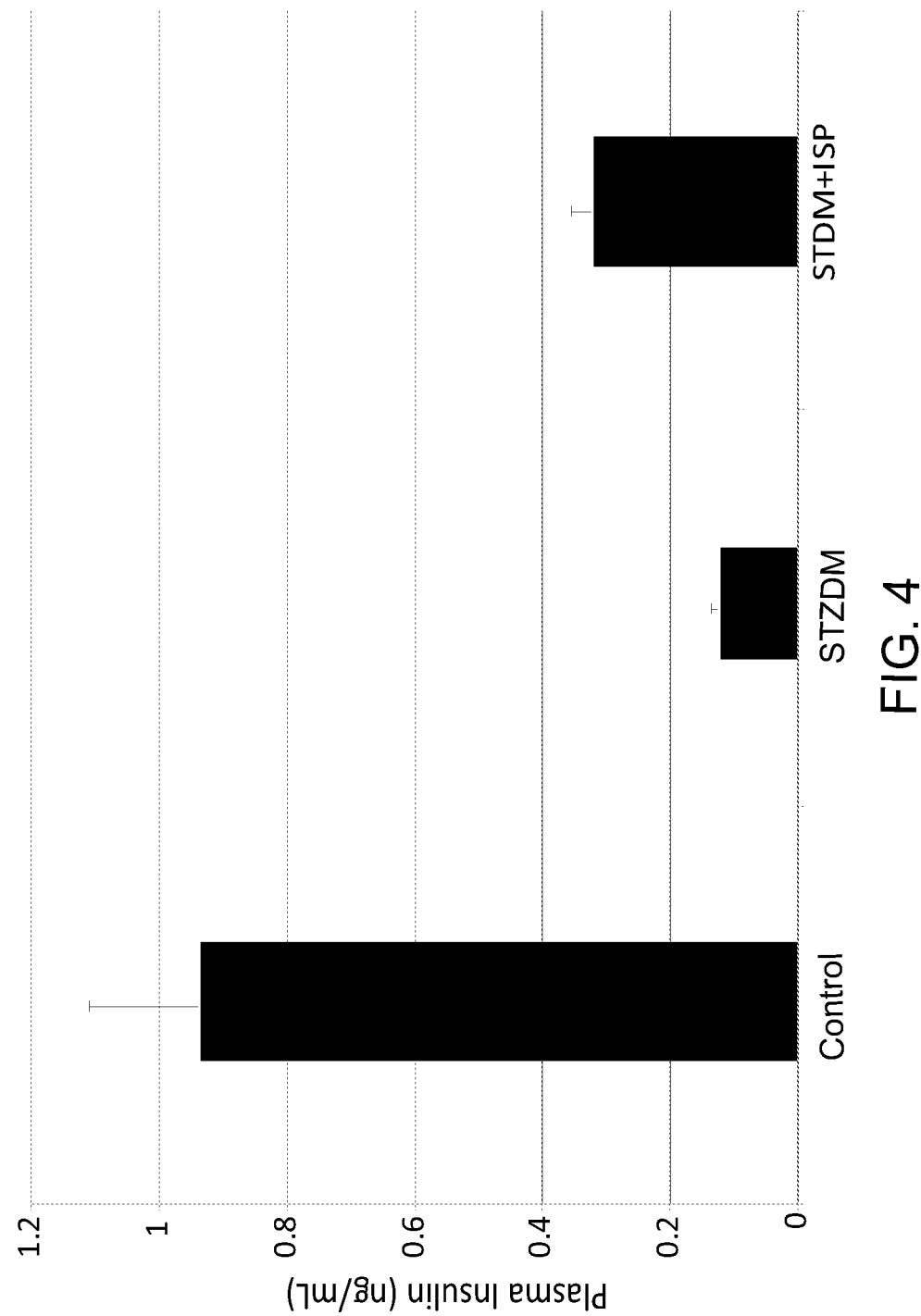
FIG. 4 is a bar graph plotting plasma insulin (ng/mL) measured in control normal rats (Control), rats treated with streptozotocin at time zero to induce diabetes (STZ DM), and rats treated with streptozotocin at time zero to induce diabetes followed by treatment with CRRL-090 ISP (1 pmol/kg/minute) for one month starting two months after streptozotocin treatment (STZ DM+ISP). For each group, the plasma insulin measurements were made using plasma samples obtained three months after the streptozotocin treatment.
Figure 5:
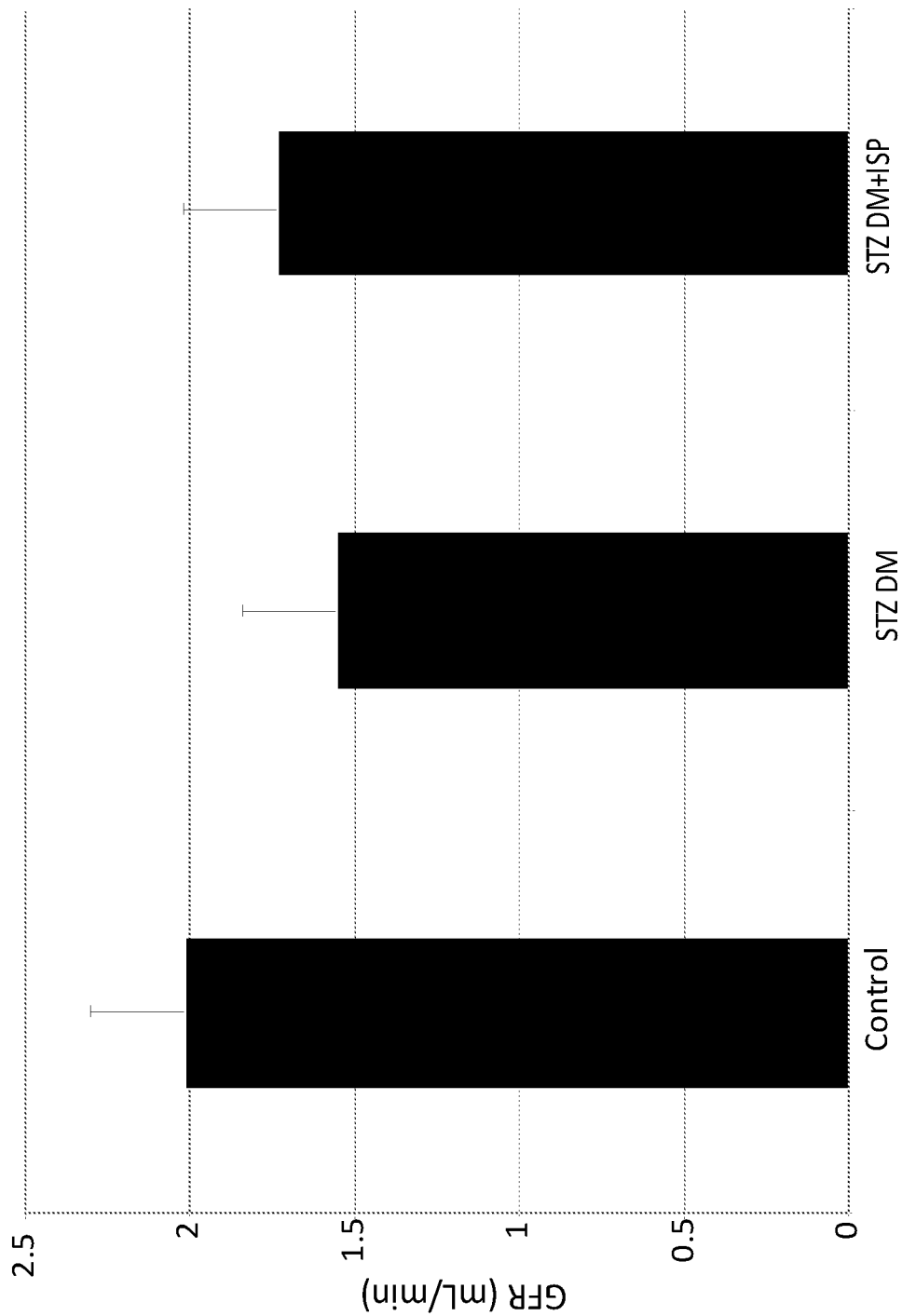
FIG. 5 is a bar graph plotting glomerular filtration rate (GFR; mL/minute) measured in control normal rats (Control), rats treated with streptozotocin at time zero to induce diabetes (STZ DM), and rats treated with streptozotocin at time zero to induce diabetes followed by treatment with CRRL-090 ISP (1 pmol/kg/minute) for one month starting two months after streptozotocin treatment (STZ DM+ISP). For each group, the glomerular filtration rate measurements were made three months after the streptozotocin treatment.
Figure 6:
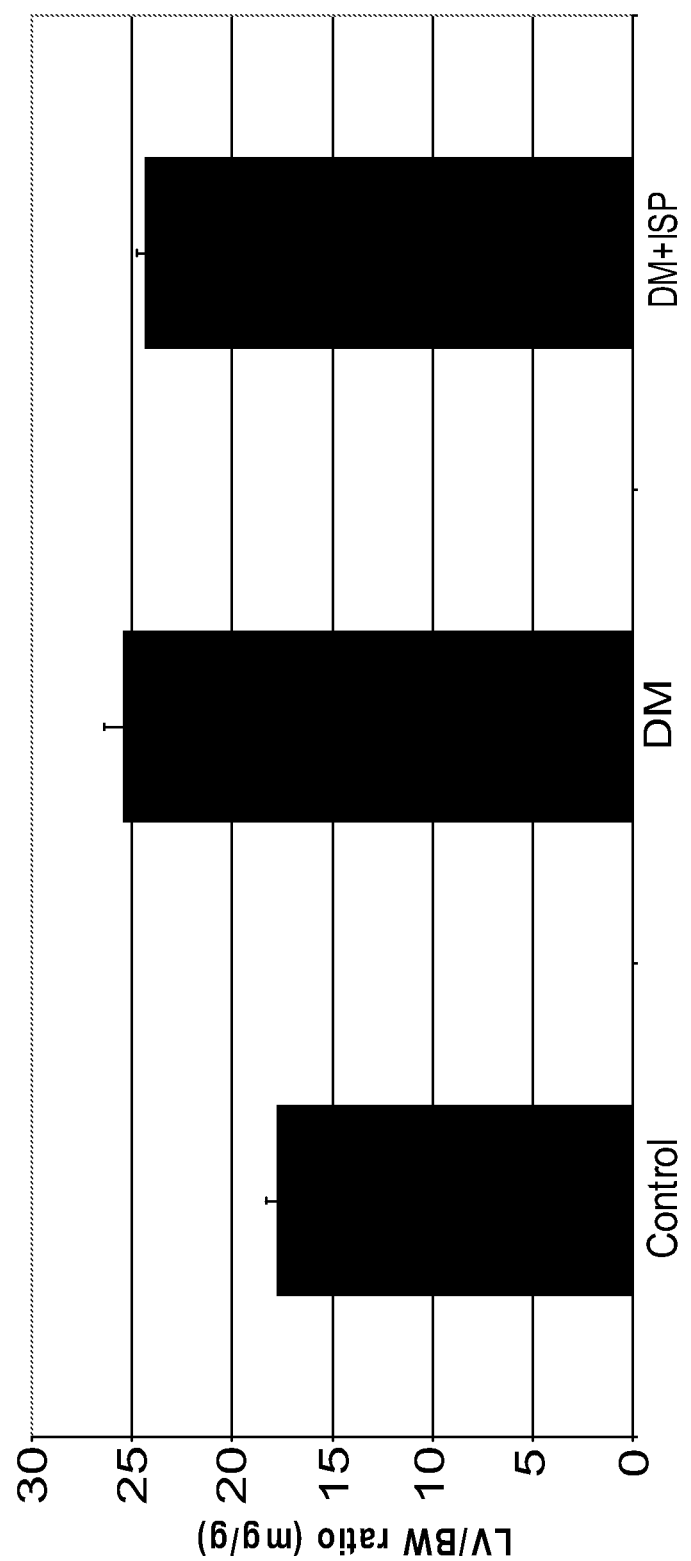
FIG. 6 is a bar graph plotting left ventricular weight to body weight ratio (LV/BW ratio; mg/g) measured in control normal rats (Control), rats treated with streptozotocin at time zero to induce diabetes (DM), and rats treated with streptozotocin at time zero to induce diabetes followed by treatment with CRRL-090 ISP (1 pmol/kg/minute) for one month starting two months after streptozotocin treatment (DM+ISP). For each group, the LV/BW measurements were made three months after the streptozotocin treatment.

Normal rats receiving infusion of CRRL-090 ISP exhibited lower blood glucose levels and increased plasma insulin as compared to control rats that received saline (FIGS. 1 and 2).

These results demonstrate that CRRL-090 ISP reduces blood glucose with increased insulin secretion.

Example 2

CRRL-090 ISP Exerts Cardiorenal and Humoral Effects when Administered to Diabetic Mammals CRRL-090 ISP was synthesized by direct protein synthesis and tested for biological activity in diabetic rats as follows. Three groups of male Wistar rats (six rats per group) were used: normal control group, diabetic control group, and diabetic group treated with CRRL-090 ISP. One dose of streptozotocin was administered intraperitoneally to induce diabetes in the rats of the diabetic control group and diabetic group treated with CRRL-090 ISP. Two months after induction of diabetes, ALZET pumps (obtained from DURECT Corporation, ALZET Osmotic Pumps, P.O. Box 530, Cupertino, Calif.; Model 1007D) configured to release 0.1 µg/kg/minute of CRRL-090 ISP or saline as control were serially implanted subcutaneously every 14 days over the course of one month (2 pumps, one on day 0 and another on day 14). Cardiac function was assessed by echocardiography, neurohormones were measured by radioimmunoassays. Fibrosis was determined by picrosirius red staining.

As compared to diabetic controls, the diabetic rats treated with CRRL-090 ISP exhibited reduced blood glucose levels, increased plasma insulin levels, an increased glomerular filtration rate (GFR), and less left ventricular hypertrophy (FIGS. 3-6).

These results demonstrate that CRRL-090 ISP can be used to increase insulin secretion in a manner that reduces blood glucose levels and improves cardiorenal function in diabetic mammals.

Example 3

Chimeric Polypeptides have Particulate Guanylate Cyclase Activating and Insulin Secreting Properties in Dogs The following was performed to define the effects of CRRL-092 ISP-NP, CRRL-093 ISP-NP, and CRRL-094 ISP-NP polypeptides on blood glucose, plasma insulin, and plasma cGMP in normal dogs (n=2). CRRL-092 ISP-NP, CRRL-093 ISP-NP, and CRRL-094 ISP-NP polypeptides were synthesized by direct protein synthesis and infused intravenously at 10 pmol/kg/minute or 100 pmol/kg/minute into normal dogs for 45 minutes after a base line measurement. After 45 minutes of infusion, a wash out period of 30 minute was performed. Blood samples were collected at the end of each period.

Figure 7:
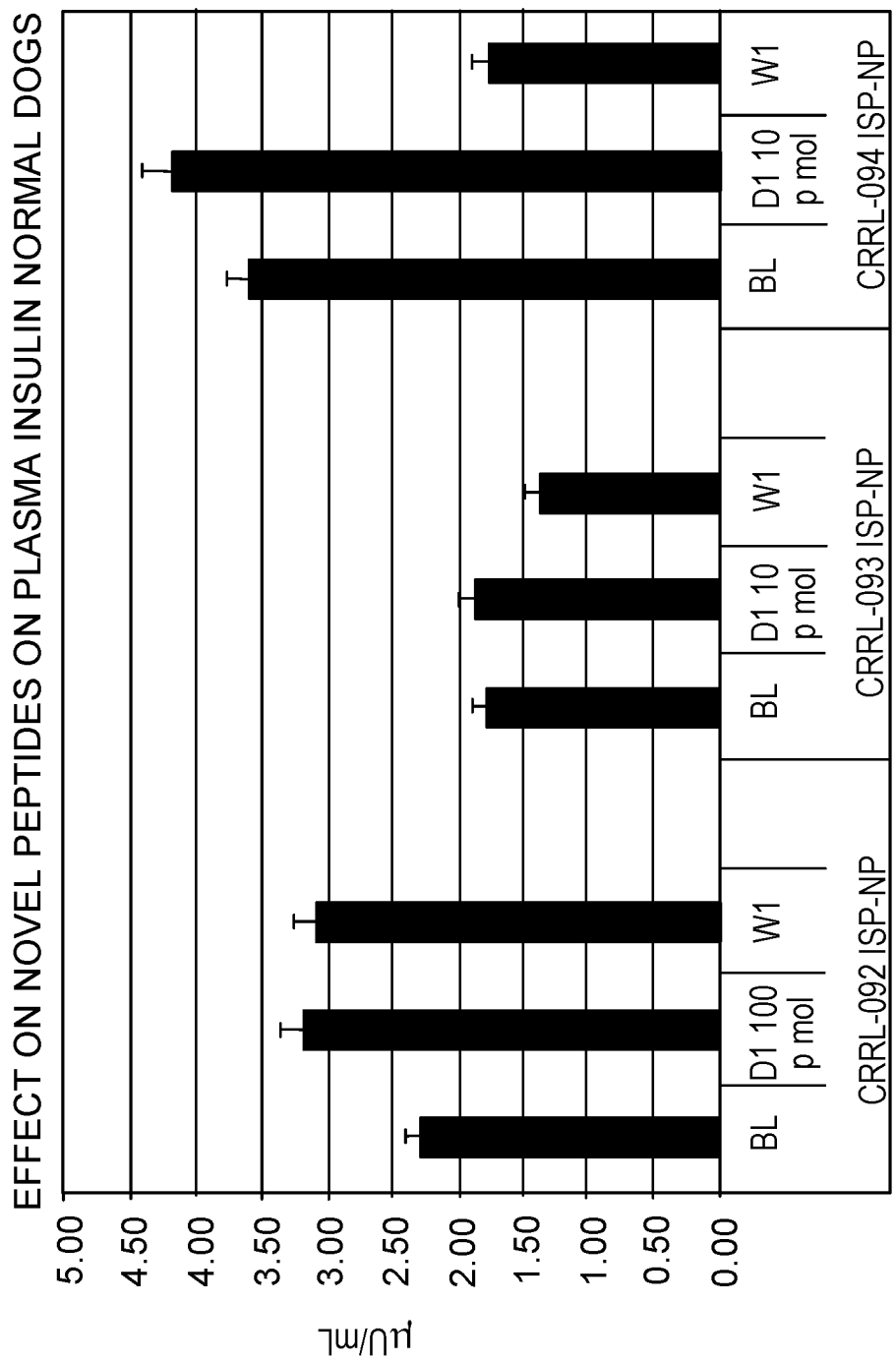
FIG. 7 is a graph plotting plasma insulin levels (µU/mL) in normal dogs measured after a 30 minute base line period (BL), measured after a 45 minute infusion period with the indicated polypeptide (D1; amounts in pmol), or measured after a 30 minute wash out period (W1).
Figure 8:
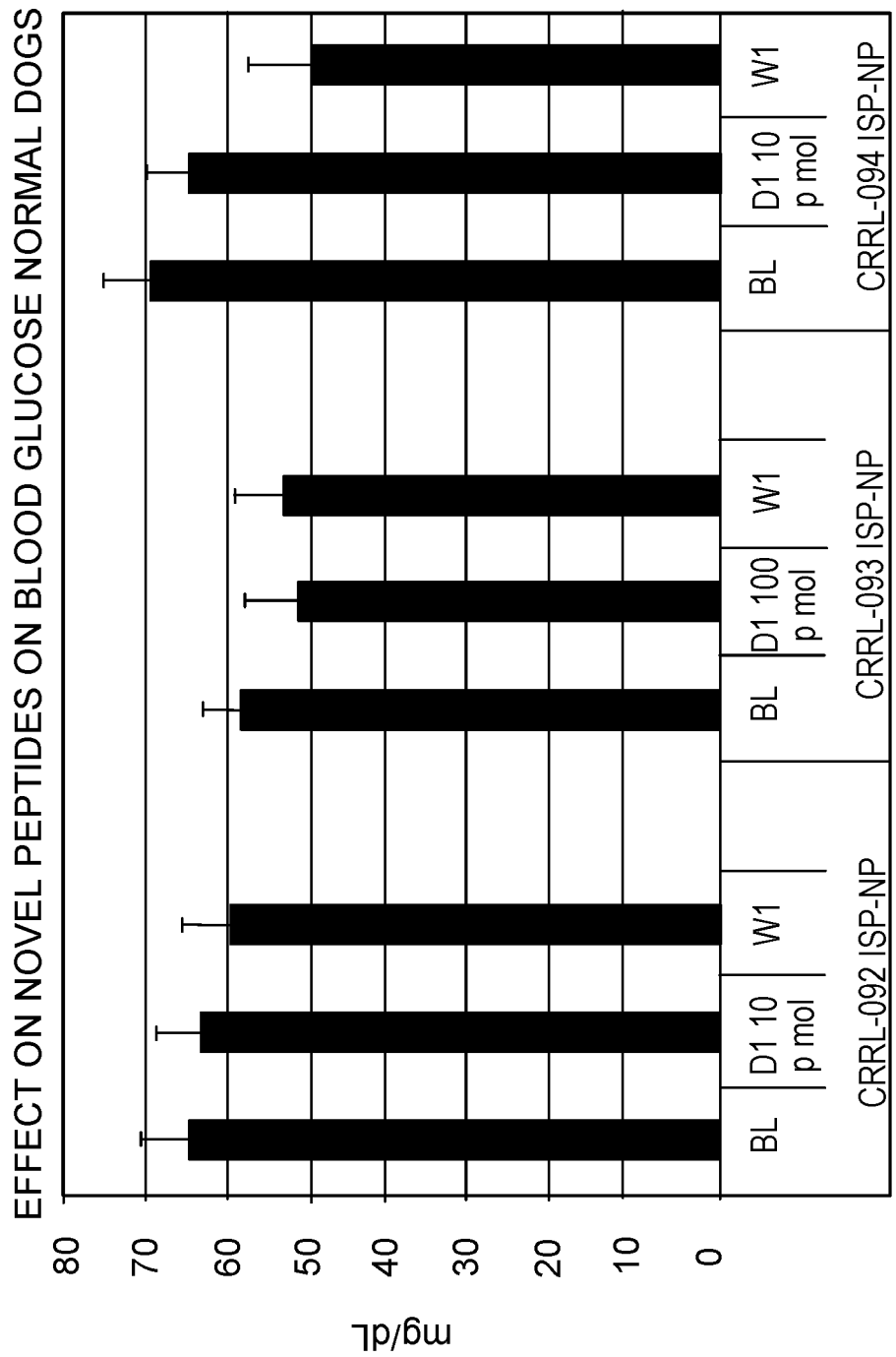
FIG. 8 is a graph plotting blood glucose levels (mg/dL) in normal dogs measured after a 30 minute base line period (BL), measured after a 45 minute infusion period with the indicated polypeptide (D1; amounts in pmol), or measured after a 30 minute wash out period (W1).
Figure 9:
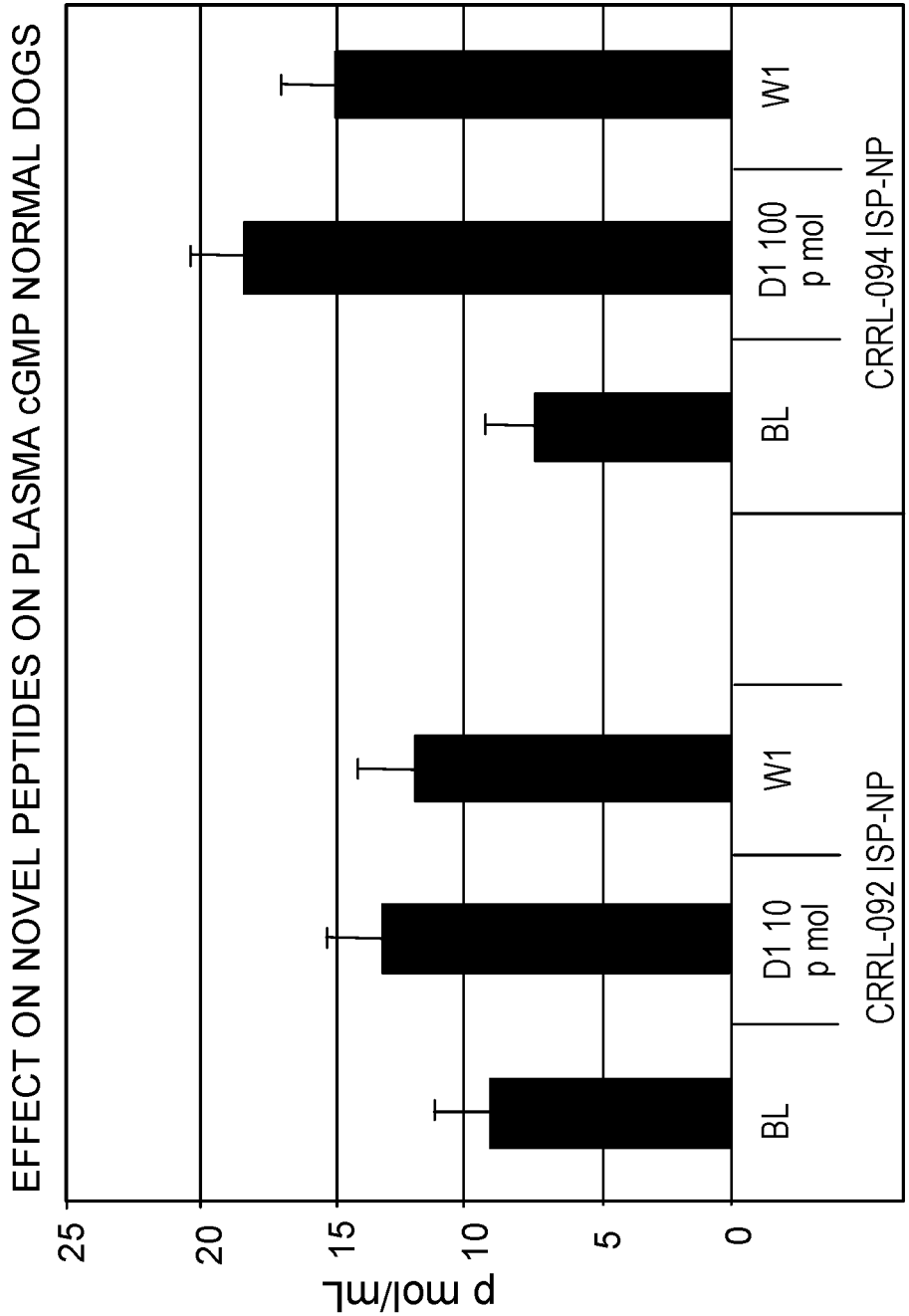
FIG. 9 is a graph plotting plasma cGMP levels (pmol/mL) in normal dogs measured after a 30 minute base line period (BL), measured after a 45 minute infusion period with the indicated polypeptide (D1; amounts in pmol), or measured after a 30 minute wash out period (W1).
Figure 10:
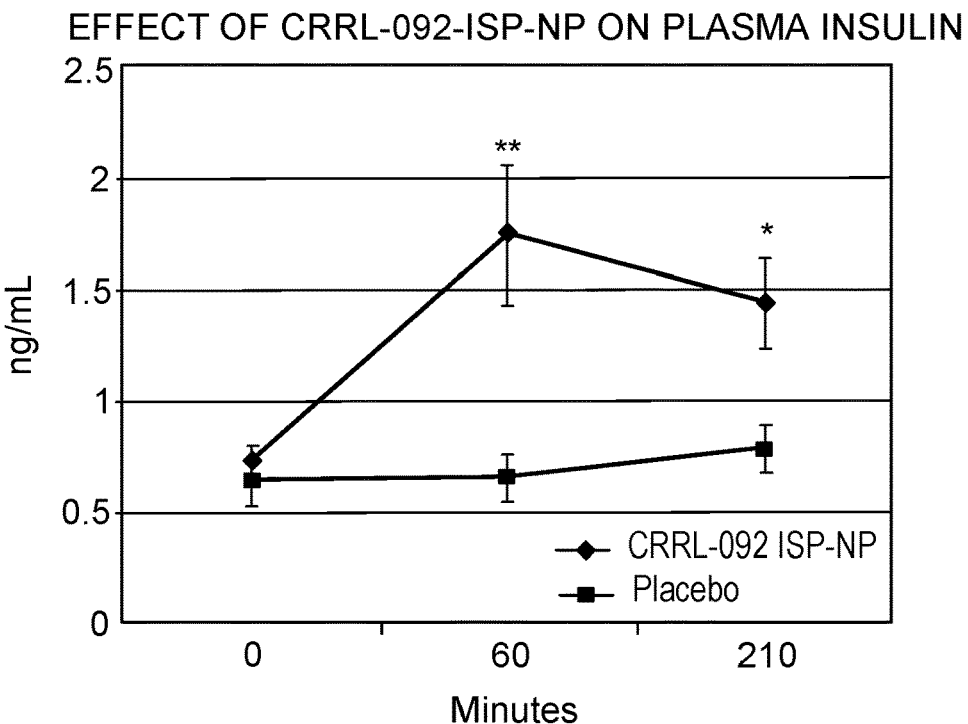
FIG. 10 is a graph plotting plasma insulin levels (ng/mL) at 0, 60, and 210 minutes of infusion in control rats and rats treated with the CRRL-092 ISP-NP polypeptide.
Figure 11:
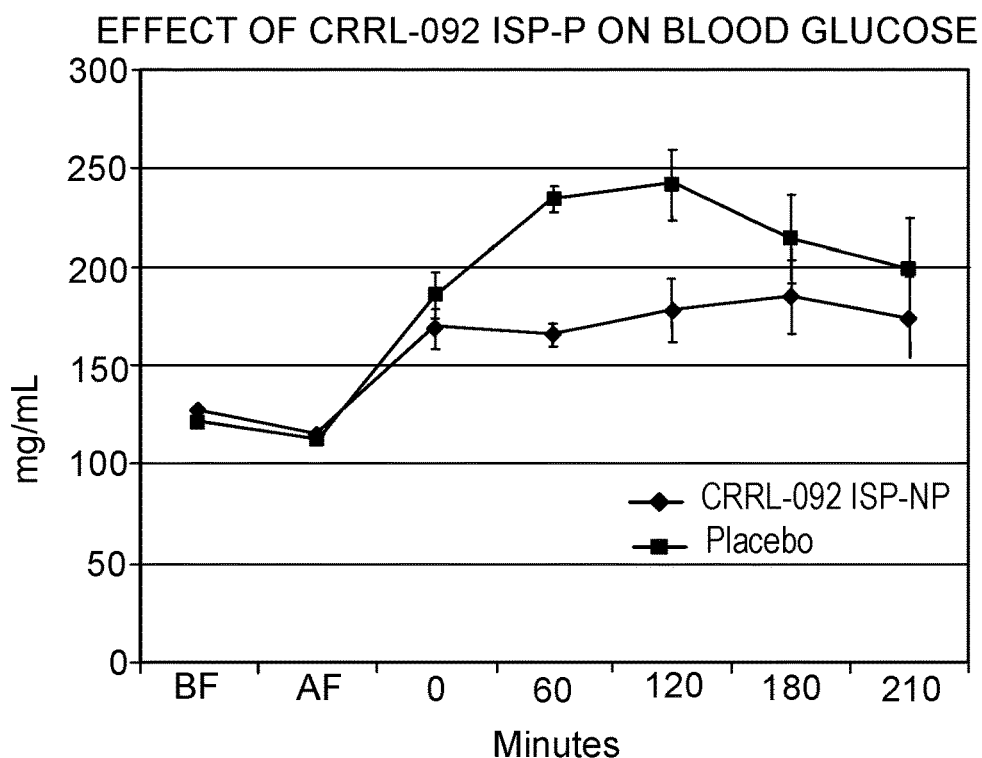
FIG. 11 is a graph plotting blood glucose levels (mg/dL) before anesthesia (BF), after anesthesia (AF), and at 0, 60, 120, 180, and 210 minutes of infusion in control rats and rats treated with the CRRL-092 ISP-NP polypeptide.
Figure 12:
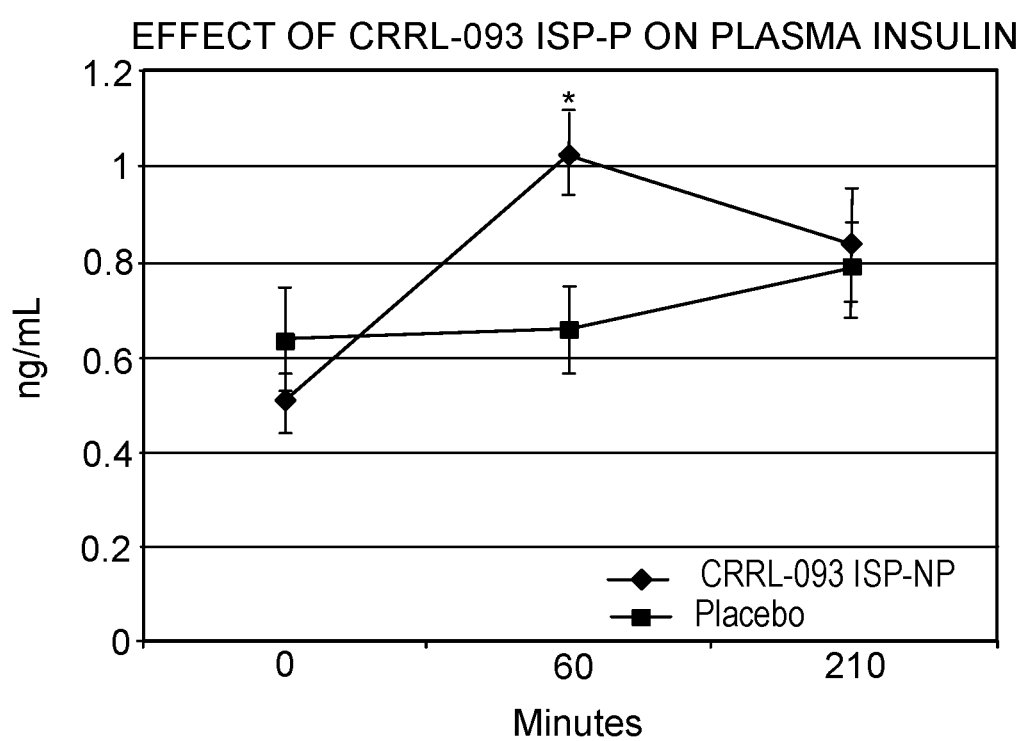
FIG. 12 is a graph plotting plasma insulin levels (ng/mL) at 0, 60, and 210 minutes of infusion in control rats and rats treated with the CRRL-093 ISP-NP polypeptide.
Figure 13:
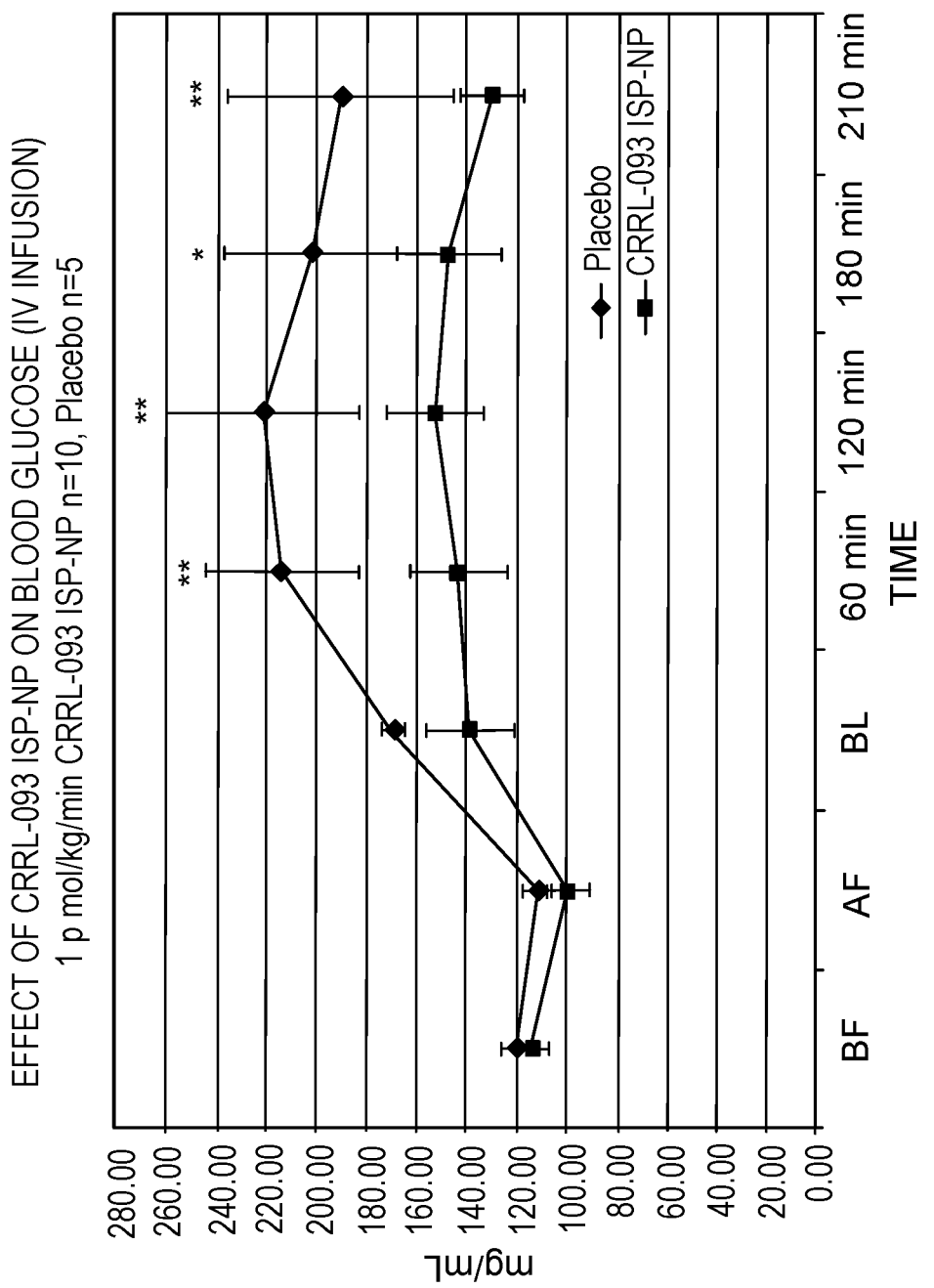
FIG. 13 is a graph plotting blood glucose levels (mg/dL) before anesthesia (BF), after anesthesia (AF), and at 60, 120, 180, and 210 minutes of infusion in control rats and rats treated with the CRRL-093 ISP-NP polypeptide.

CRRL-092 ISP-NP, CRRL-093 ISP-NP, and CRRL-094 ISP-NP polypeptide infusion resulted in an increase in plasma insulin and cGMP with a reduction in plasma glucose (FIGS. 7-9). These results demonstrate that chimeric polypeptides that include at least one amino acid segment (e.g., N-terminus tail, ring structure, C-terminus tail, or a combination thereof) of a natriuretic peptide (e.g., ANP, BNP, CNP, URO, or DNP) and an amino acid segment that includes either the amino acid sequence set forth in SEQ ID NO:1 or the amino acid sequence set forth in SEQ ID NO:1 with the exception that it contains one, two, three, four, or five amino acid additions, subtractions, or substitutions can exhibit particulate guanylate cyclase activating and insulin secreting properties in vivo.

Example 4

Chimeric Polypeptides have Particulate Guanylate Cyclase Activating and Insulin Secreting Properties in Rats The following was performed to define the effects of CRRL-092 ISP-NP and CRRL-093 ISP-NP polypeptides on blood glucose and plasma insulin in normal rats. In one experiment, seven normal rats received normal saline, four normal rats received IV infusion of the CRRL-092 ISP-NP polypeptide at 1 pmol/kg/minute for 210 minutes, and three normal rats received IV bolus of CRRL-092 ISP-NP polypeptide at 100 pmol/kg. In another experiment, five normal rats received normal saline, and ten normal rats received IV infusion of the CRRL-093 ISP-NP polypeptide at 1 pmol/kg/minute for 210 minutes.

Normal rats receiving infusion CRRL-092 ISP-NP and CRRL-093 ISP-NP polypeptides exhibited lower blood glucose and increased plasma insulin as compared to placebo control rats (FIGS. 10-13). These results demonstrate that chimeric polypeptides that include at least one amino acid segment (e.g., N-terminus tail, ring structure, C-terminus tail, or a combination thereof) of a natriuretic peptide (e.g., ANP, BNP, CNP, URO, or DNP) and an amino acid segment that includes either the amino acid sequence set forth in SEQ ID NO:1 or the amino acid sequence set forth in SEQ ID NO:1 with the exception that it contains one, two, three, four, or five amino acid additions, subtractions, or substitutions can exhibit particulate guanylate cyclase activating and insulin secreting properties in vivo.

Example 5

Assessing Chimeric Polypeptides Having Guanylate Cyclase Activating Properties

The following was performed to determine if CRRL-092 ISP-NP, CRRL-093 ISP-NP, CRRL-094 ISP-NP, and CRRL-095 ISP-NP polypeptides activate GC-A particulate guanylate cyclase receptors or GC-B particulate guanylate cyclase receptors to produce the second messenger cGMP.

Human embryonic kidney 293 (HEK293) cells were stably transfected with either GC-A or GC-B using Lipofectamine (Invitrogen, Grand Island, N.Y.). Transfected cells were maintained in Dulbecco's modified Eagle's medium supplemented with 10% fetal bovine serum, 100 U/ml penicillin, 100 U/ml streptomycin, and 250m/m1 G418 (all reagents from Invitrogen, Grand Island, N.Y.).

To perform the cell cGMP assay, cells were plated in 6-well plates and treated as described elsewhere (Tsuruda et al., Circ. Res, 91:1127-1134 (2002)). Briefly, cells were incubated in Hank's balanced salt solution (Invitrogen, Carlsbad, Calif.) containing 20 mmol/L N-[2-hydroxyethyl]piperazine-N'[2-ethanesulfonic acid], 0.1% bovine serum albumin, and 0.5 mmol/L 3-isobutyl-1-methylxanthine (Sigma, St. Louis, Mo.). Treated cells received $10^{-6}$M, $10^{-8}$M, or $10^{10}$M polypeptide for 10 minutes. Cells were lysed in 300 µL 6% TCA and sonicated for 10 minutes. The samples were ether extracted four times in 4 volumes of ether, dried, and reconstituted in 300 µL cGMP assay buffer. The samples were assayed using a competitive RIA cGMP kit (Perkin-Elmer, Boston, Mass.) as described elsewhere (Tsuruda et al., Circ. Res, 91:1127-1134 (2002)).

Figure 14:
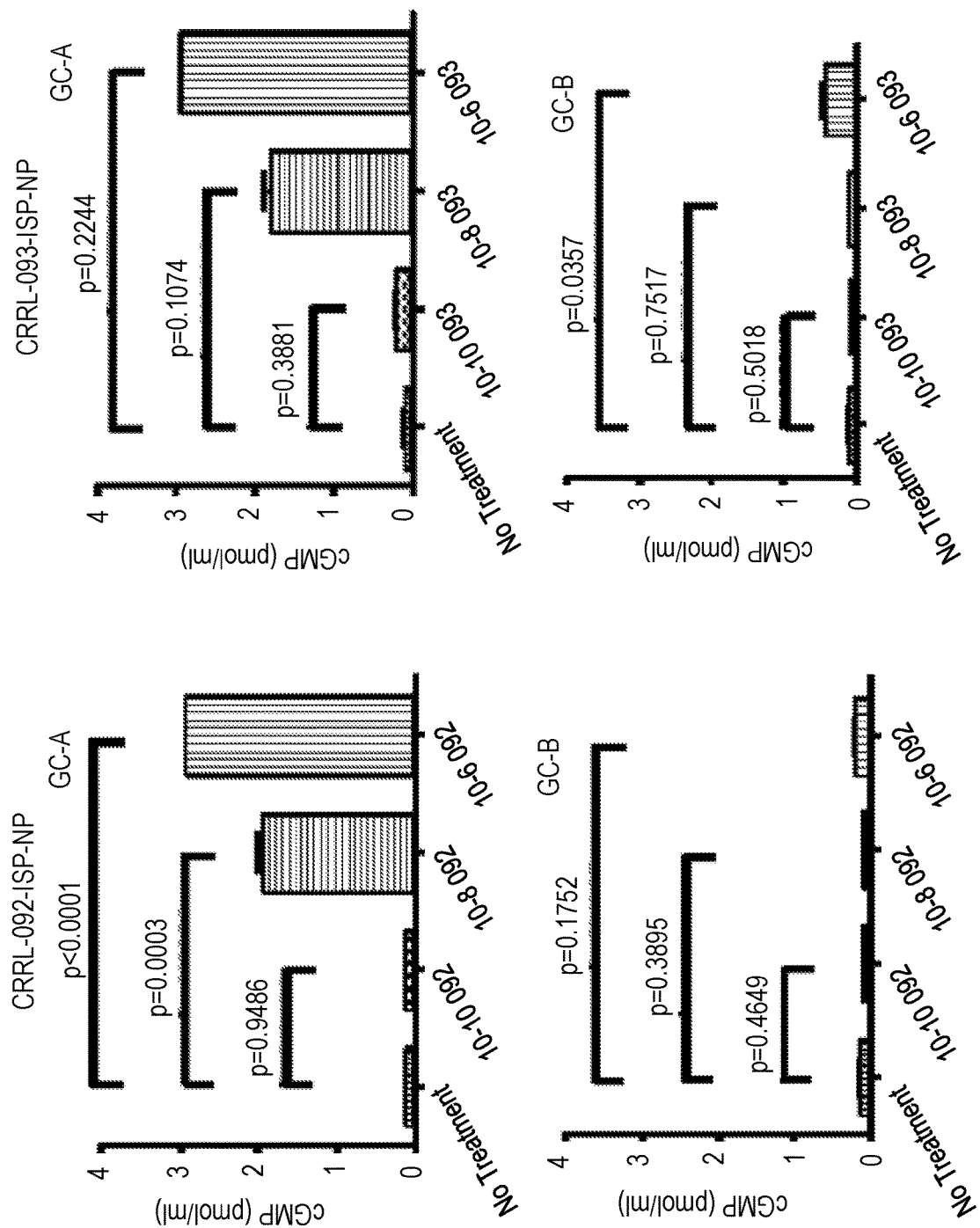
FIG. 14 contains graphs plotting the cGMP levels (pmol/mL) for GC-A receptor cells or GC-B receptor cells exposed to no treatment or treatment with $10^{-10}$ M, $10^{-8}$M, or $10^{-6}$M of the CRRL-092 ISP-NP polypeptide or the CRRL-093 ISP-NP polypeptide.

CRRL-092 ISP-NP and CRRL-093 ISP-NP polypeptides activated the GC-A receptors, but not the GC-B receptors (FIG. 14). CRRL-094 ISP-NP and CRRL-095 ISP-NP polypeptides activated both the GC-A and GC-B receptors (FIG. 15).

These results demonstrate that while CRRL-092 ISP-NP and CRRL-093 ISP-NP activate the GC-A receptor only, CRRL-094 ISP-NP and CRRL-095 ISP-NP polypeptides activate both the GC-A and GC-B receptors.

Example 6

Chronic Therapy with CRRL-094 ISP-NP Activates cGMP, Increases Insulin Secretion, and Lowers Blood Glucose and Body Weight Three groups of male Wistar rats were used: (1) normal non-diabetic control rats, (2) diabetic control rats, and (3) diabetic rats treated with CRRL-094 ISP-NP. Two months after induction of diabetes, ALZET pumps (obtained from DURECT Corporation, ALZET Osmotic Pumps, P.O. Box 530, Cupertino, Calif.; Model 1007D) filled with CRRL-094 ISP-NP in saline (dose=1 pmol/kg/minute) or saline as control were serially implanted subcutaneously every 14 days over the course of one month. After four weeks of treatment, blood glucose levels, plasma insulin levels, body weight, plasma and urine cGMP levels, and left ventricular hypertrophy were measured. Blood glucose levels and body weight also were measured after two weeks of treatment.

Figure 16:
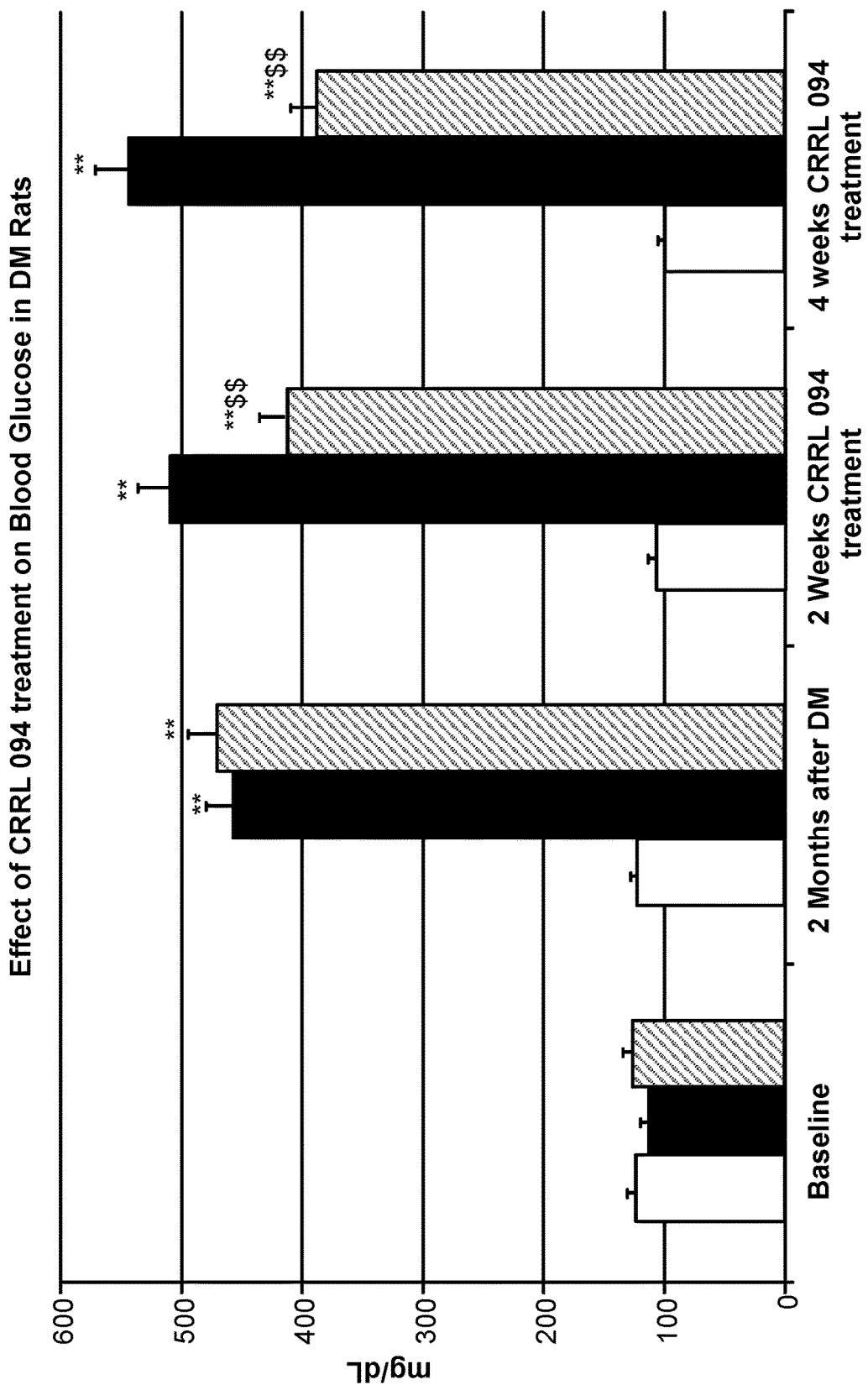
FIG. 16 is a graph plotting blood glucose levels (mg/dL) measured in normal non-diabetic control rats treated with saline (normal control), diabetic control rats treated with saline (diabetic control), and diabetic rats treated with CRRL-094 ISP-NP (DM+CRRL 094) at baseline, after inducing diabetes for two months, after two weeks of saline or CRRL-094 ISP-NP treatment, or after four weeks of saline or CRRL-094 ISP-NP treatment.  indicates $p<0.05$ versus Normal Control; $$ indicates $p<0.05$ versus Diabetic Control.
Figure 17:
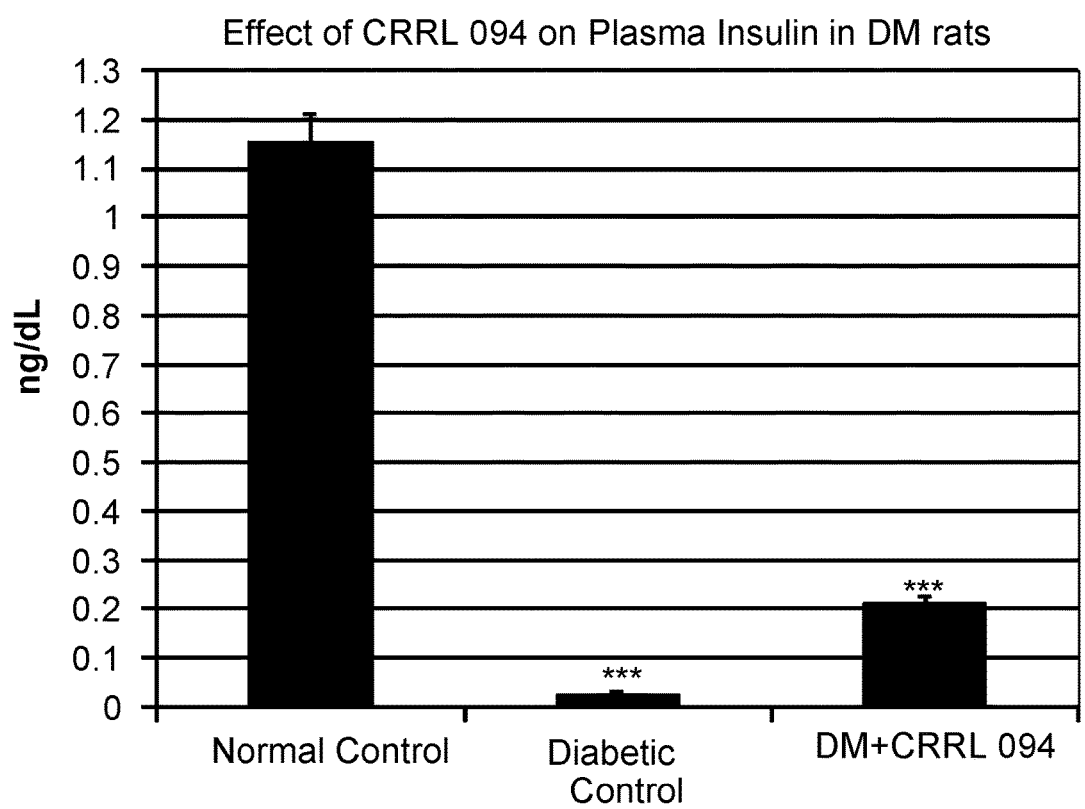
FIG. 17 is a graph plotting plasma insulin levels (ng/mL) measured in normal non-diabetic control rats treated with saline (normal control), diabetic control rats treated with saline (diabetic control), and diabetic rats treated with CRRL-094 ISP-NP (DM+CRRL 094) after four weeks of saline or CRRL-094 ISP-NP treatment.
Figure 18:
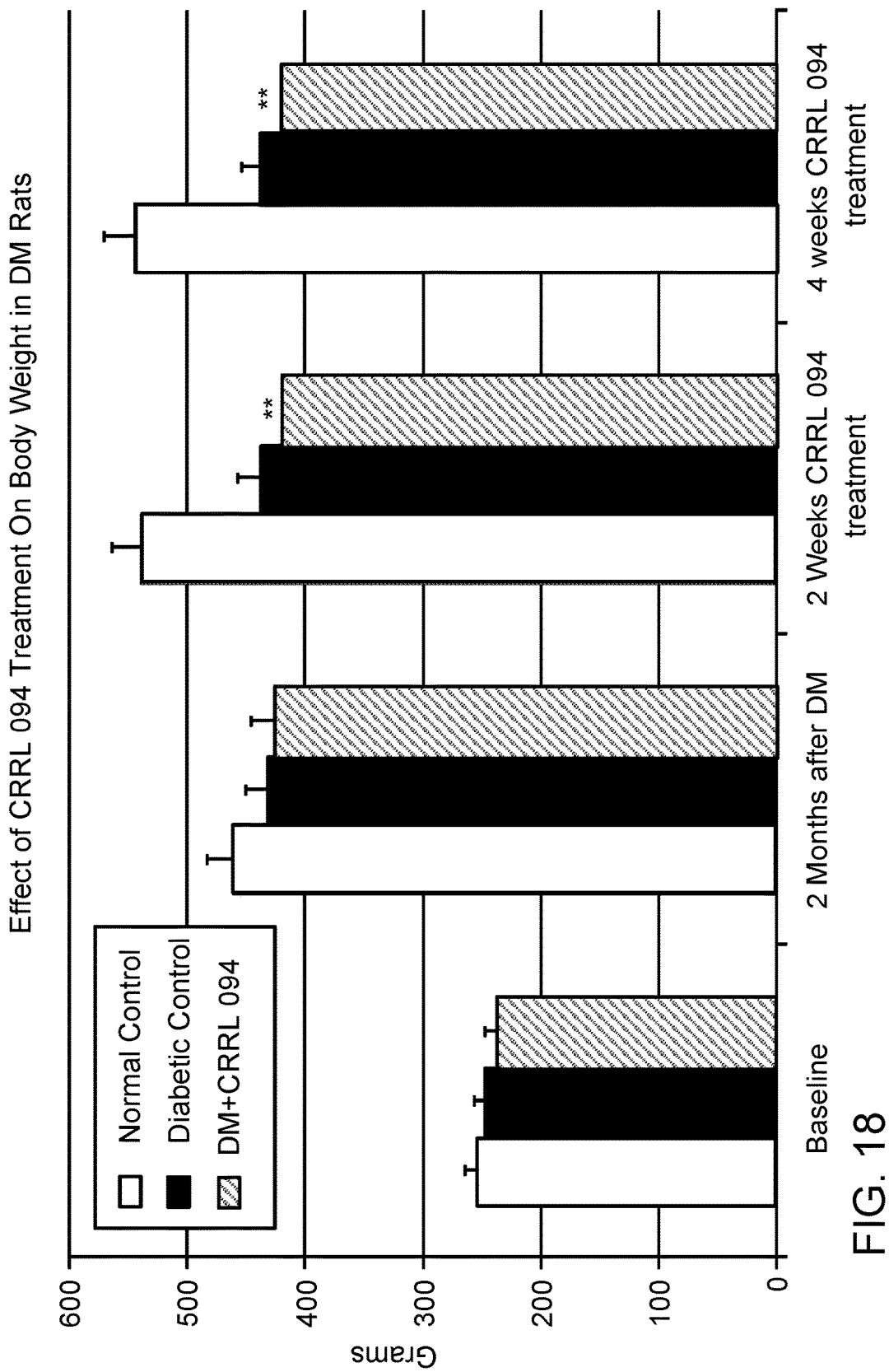
FIG. 18 is a graph plotting body weight (grams) measured in normal non-diabetic control rats treated with saline (normal control), diabetic control rats treated with saline (diabetic control), and diabetic rats treated with CRRL-094 ISP-NP (DM+CRRL 094) at baseline, after inducing diabetes for two months, after two weeks of saline or CRRL-094 ISP-NP treatment, or after four weeks of saline or CRRL-094 ISP-NP treatment. ** indicates $p<0.05$ versus Normal Control.
Figure 19:
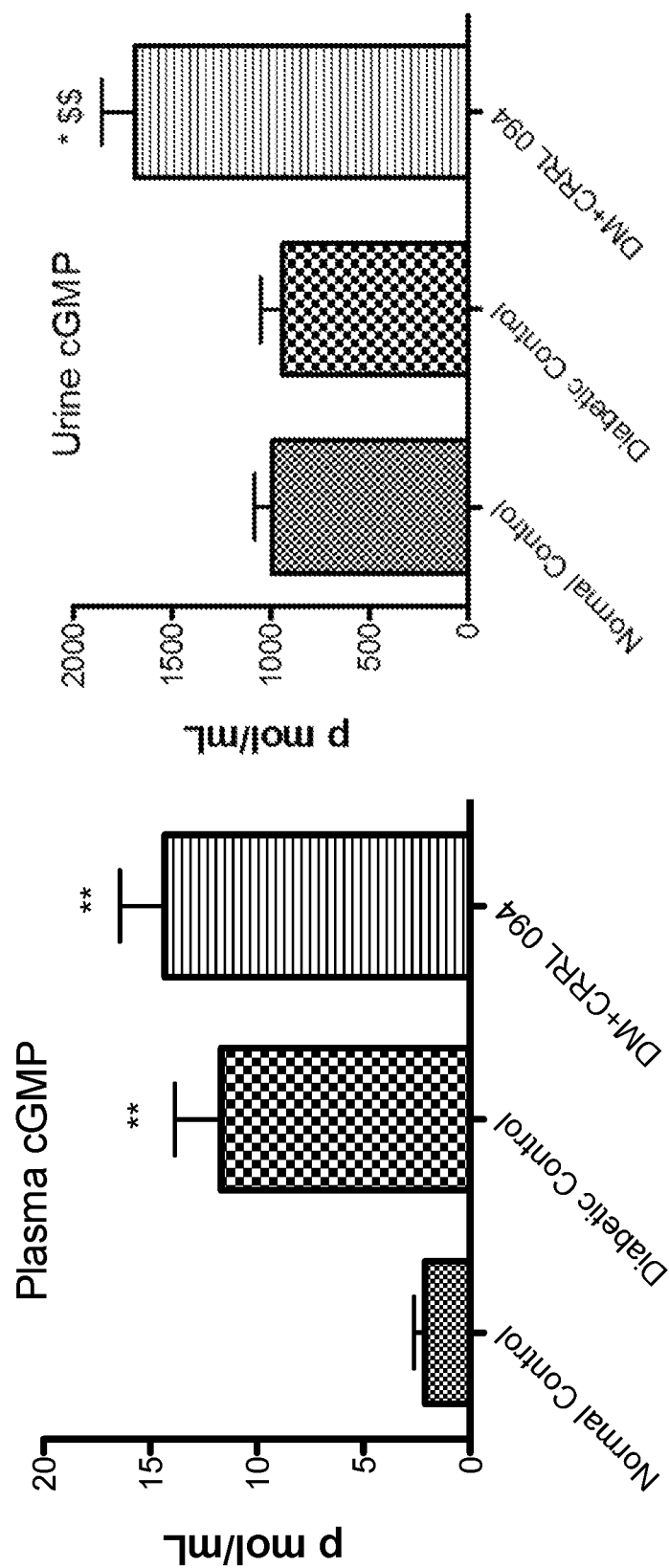
FIG. 19 contains graphs plotting plasma cGMP and urine cGMP levels (pmol/mL) measured in normal non-diabetic control rats treated with saline (normal control), diabetic control rats treated with saline (diabetic control), and diabetic rats treated with CRRL-094 ISP-NP (DM+CRRL 094) after four weeks of saline or CRRL-094 ISP-NP treatment.

As compared to the diabetic rats treated with the saline control, diabetic rats treated with CRRL-094 ISP-NP exhibited reduced blood glucose (FIG. 16), increased plasma insulin (FIG. 17), reduced body weight (FIG. 18), increased plasma and urine cGMP (FIG. 19), and reduced left ventricular hypertrophy (FIG. 20). These results demonstrate that four weeks of chronic treatment with CRRL-094 ISP-NP results in increased insulin secretion that results in lower blood glucose and body weight in a rodent model of diabetes. Chronic treatment with CRRL-094 ISP-NP also activated the cGMP system, which resulted in decrease left ventricular hypertrophy. Thus, CRRL-094 ISP-NP exhibited both insulin secreting and cGMP activating properties. These results also demonstrate that CRRL-094 ISP-NP can be used to treat or control hyperglycemia and protect cardiovascular and renal function in mammals suffering from diabetes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inducing insulin secretion or treating diabetes, wherein said method comprises administering a composition comprising a polypeptide consisting of the sequence set forth in SEQ ID NO:11 to a mammal.

2. The method of claim 1, wherein said mammal is a human.

* * * * *

SEQUENCE LISTING

<160> NUMBER OF SEQ ID NOS: 18

<210> SEQ ID NO 1
<211> LENGTH: 18
<212> TYPE: PRT
<213> ORGANISM: Artificial Sequence
<220> FEATURE:
<223> OTHER INFORMATION: synthetic peptide

<400> SEQUENCE: 1

His Gly Glu Gly Thr Phe Thr Ser Asp Ser Glu Ala Phe Ile Trp Leu
1               5                   10                  15

Gly Arg

<210> SEQ ID NO 2
<211> LENGTH: 49
<212> TYPE: PRT
<213> ORGANISM: Artificial Sequence
<220> FEATURE:
<223> OTHER INFORMATION: synthetic peptide

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
                20                  25                  30

Gly Glu Gly Thr Phe Thr Ser Asp Ser Glu Ala Phe Ile Trp Leu Gly
            35                  40                  45

Arg

<210> SEQ ID NO 3
<211> LENGTH: 50
<212> TYPE: PRT
<213> ORGANISM: Artificial Sequence
<220> FEATURE:
<223> OTHER INFORMATION: synthetic peptide

<400> SEQUENCE: 3

His Gly Glu Gly Thr Phe Thr Ser Asp Ser Glu Ala Phe Ile Trp Leu
1               5                   10                  15

Gly Arg Ser Pro Lys Met Val Gln Gly Ser Gly Cys Phe Gly Arg Lys
                20                  25                  30

Met Asp Arg Ile Ser Ser Ser Ser Gly Leu Gly Cys Lys Val Leu Arg
            35                  40                  45

Arg His
    50

<210> SEQ ID NO 4
<211> LENGTH: 51
<212> TYPE: PRT
<213> ORGANISM: Artificial Sequence
<220> FEATURE:
<223> OTHER INFORMATION: synthetic peptide

<400> SEQUENCE: 4

His Gly Glu Gly Thr Phe Thr Ser Asp Ser Glu Ala Phe Ile Trp Leu
1               5                   10                  15

Gly Arg Arg Met Asp Arg Ile Gly Leu Ser Lys Gly Cys Phe Gly Leu
                20                  25                  30

Lys Leu Asp Arg Ile Gly Ser Met Ser Gly Leu Gly Cys Lys Val Leu
            35                  40                  45

Arg Arg His
    50

<210> SEQ ID NO 5
<211> LENGTH: 51
<212> TYPE: PRT
<213> ORGANISM: Artificial Sequence
<220> FEATURE:
<223> OTHER INFORMATION: synthetic peptide

<400> SEQUENCE: 5

Arg Met Asp Arg Ile Gly Leu Ser Lys Gly Cys Phe Gly Leu Lys Leu
1               5                   10                  15

Asp Arg Ile Gly Ser Met Ser Gly Leu Gly Cys Lys Val Leu Arg Arg
            20                  25                  30

His His Gly Glu Gly Thr Phe Thr Ser Asp Ser Glu Ala Phe Ile Trp
        35                  40                  45

Leu Gly Arg
    50

<210> SEQ ID NO 6
<211> LENGTH: 50
<212> TYPE: PRT
<213> ORGANISM: Artificial Sequence
<220> FEATURE:
<223> OTHER INFORMATION: synthetic peptide

<400> SEQUENCE: 6

Arg Met Asp Arg Ile Gly Leu Ser Lys Gly Cys Phe Gly Leu Lys Leu
1               5                   10                  15

Asp Arg Ile Gly Ser Met Ser Gly Leu Gly Cys Lys Val Leu Arg Arg
            20                  25                  30

His Gly Glu Gly Thr Phe Thr Ser Asp Ser Glu Ala Phe Ile Trp Leu
        35                  40                  45

Gly Arg
    50

<210> SEQ ID NO 7
<211> LENGTH: 46
<212> TYPE: PRT
<213> ORGANISM: Artificial Sequence
<220> FEATURE:
<223> OTHER INFORMATION: synthetic peptide

<400> SEQUENCE: 7

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr His Gly Glu Gly
            20                  25                  30

Thr Phe Thr Ser Asp Ser Glu Ala Phe Ile Trp Leu Gly Arg
        35                  40                  45

<210> SEQ ID NO 8
<211> LENGTH: 46
<212> TYPE: PRT
<213> ORGANISM: Artificial Sequence
<220> FEATURE:
<223> OTHER INFORMATION: synthetic peptide

<400> SEQUENCE: 8

His Gly Glu Gly Thr Phe Thr Ser Asp Ser Glu Ala Phe Ile Trp Leu
1               5                   10                  15

Gly Arg Ser Leu Arg Arg Ser Ser Cys Phe Gly Gly Arg Met Asp Arg
            20                  25                  30

Ile Gly Ala Gln Ser Gly Leu Gly Cys Asn Ser Phe Arg Tyr
        35                  40                  45

```
<210> SEQ ID NO 9
<211> LENGTH: 40
<212> TYPE: PRT
<213> ORGANISM: Artificial Sequence
<220> FEATURE:
<223> OTHER INFORMATION: synthetic peptide

<400> SEQUENCE: 9

Gly Leu Ser Lys Gly Cys Phe Gly Leu Lys Leu Asp Arg Ile Gly Ser
1               5                   10                  15

Met Ser Gly Leu Gly Cys His Gly Glu Gly Thr Phe Thr Ser Asp Ser
            20                  25                  30

Glu Ala Phe Ile Trp Leu Gly Arg
        35                  40

<210> SEQ ID NO 10
<211> LENGTH: 40
<212> TYPE: PRT
<213> ORGANISM: Artificial Sequence
<220> FEATURE:
<223> OTHER INFORMATION: synthetic peptide

<400> SEQUENCE: 10

His Gly Glu Gly Thr Phe Thr Ser Asp Ser Glu Ala Phe Ile Trp Leu
1               5                   10                  15

Gly Arg Gly Leu Ser Lys Gly Cys Phe Gly Leu Lys Leu Asp Arg Ile
            20                  25                  30

Gly Ser Met Ser Gly Leu Gly Cys
        35                  40

<210> SEQ ID NO 11
<211> LENGTH: 56
<212> TYPE: PRT
<213> ORGANISM: Artificial Sequence
<220> FEATURE:
<223> OTHER INFORMATION: synthetic peptide

<400> SEQUENCE: 11

Glu Val Lys Tyr Asp Pro Cys Phe Gly His Lys Ile Asp Arg Ile Asn
1               5                   10                  15

His Val Ser Asn Leu Gly Cys Pro Ser Leu Arg Asp Pro Arg Pro Asn
            20                  25                  30

Ala Pro Ser Thr Ser Ala His Gly Glu Gly Thr Phe Thr Ser Asp Ser
        35                  40                  45

Glu Ala Phe Ile Trp Leu Gly Arg
    50                  55

<210> SEQ ID NO 12
<211> LENGTH: 56
<212> TYPE: PRT
<213> ORGANISM: Artificial Sequence
<220> FEATURE:
<223> OTHER INFORMATION: synthetic peptide

<400> SEQUENCE: 12

His Gly Glu Gly Thr Phe Thr Ser Asp Ser Glu Ala Phe Ile Trp Leu
1               5                   10                  15
```

```
Gly Arg Glu Val Lys Tyr Asp Pro Cys Phe Gly His Lys Ile Asp Arg
            20                  25                  30

Ile Asn His Val Ser Asn Leu Gly Cys Pro Ser Leu Arg Asp Pro Arg
            35                  40                  45

Pro Asn Ala Pro Ser Thr Ser Ala
            50                  55

<210> SEQ ID NO 13
<211> LENGTH: 50
<212> TYPE: PRT
<213> ORGANISM: Artificial Sequence
<220> FEATURE:
<223> OTHER INFORMATION: synthetic peptide

<400> SEQUENCE: 13

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asn Ser Phe Arg Tyr
            20                  25                  30

His Gly Glu Gly Thr Phe Thr Ser Asp Ser Glu Ala Phe Ile Trp Leu
            35                  40                  45

Gly Arg
    50

<210> SEQ ID NO 14
<211> LENGTH: 50
<212> TYPE: PRT
<213> ORGANISM: Artificial Sequence
<220> FEATURE:
<223> OTHER INFORMATION: synthetic peptide

<400> SEQUENCE: 14

His Gly Glu Gly Thr Phe Thr Ser Asp Ser Glu Ala Phe Ile Trp Leu
1               5                   10                  15

Gly Arg Thr Ala Pro Arg Ser Leu Arg Arg Ser Ser Cys Phe Gly Leu
            20                  25                  30

Lys Leu Asp Arg Ile Gly Ser Met Ser Gly Leu Gly Cys Asn Ser Phe
            35                  40                  45

Arg Tyr
    50

<210> SEQ ID NO 15
<211> LENGTH: 55
<212> TYPE: PRT
<213> ORGANISM: Artificial Sequence
<220> FEATURE:
<223> OTHER INFORMATION: synthetic peptide

<400> SEQUENCE: 15

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala His Gly Glu Gly Thr Phe Thr Ser Asp Ser Glu
            35                  40                  45
```

```
Ala Phe Ile Trp Leu Gly Arg
    50              55

<210> SEQ ID NO 16
<211> LENGTH: 55
<212> TYPE: PRT
<213> ORGANISM: Artificial Sequence
<220> FEATURE:
<223> OTHER INFORMATION: synthetic peptide

<400> SEQUENCE: 16

His Gly Glu Gly Thr Phe Thr Ser Asp Ser Glu Ala Phe Ile Trp Leu
1               5                   10                  15

Gly Arg Gly Leu Ser Lys Gly Cys Phe Gly Leu Lys Leu Asp Arg Ile
            20                  25                  30

Gly Ser Met Ser Gly Leu Gly Cys Pro Ser Leu Arg Asp Pro Arg Pro
        35                  40                  45

Asn Ala Pro Ser Thr Ser Ala
    50              55

<210> SEQ ID NO 17
<211> LENGTH: 58
<212> TYPE: PRT
<213> ORGANISM: Artificial Sequence
<220> FEATURE:
<223> OTHER INFORMATION: synthetic peptide

<400> SEQUENCE: 17

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr Arg Ile Thr Ala
            20                  25                  30

Arg Glu Asp Lys Gln Gly Trp Ala His Gly Glu Gly Thr Phe Thr Ser
        35                  40                  45

Asp Ser Glu Ala Phe Ile Trp Leu Gly Arg
    50                  55

<210> SEQ ID NO 18
<211> LENGTH: 58
<212> TYPE: PRT
<213> ORGANISM: Artificial Sequence
<220> FEATURE:
<223> OTHER INFORMATION: synthetic peptide

<400> SEQUENCE: 18

His Gly Glu Gly Thr Phe Thr Ser Asp Ser Glu Ala Phe Ile Trp Leu
1               5                   10                  15

Gly Arg Ser Leu Arg Arg Ser Ser Cys Phe Gly Gly Arg Met Asp Arg
            20                  25                  30

Ile Gly Ala Gln Ser Gly Leu Gly Cys Asn Ser Phe Arg Tyr Arg Ile
            35                  40                  45

Thr Ala Arg Glu Asp Lys Gln Gly Trp Ala
    50                  55
```